(12) United States Patent
Konakanchi et al.

(10) Patent No.: US 8,080,558 B2
(45) Date of Patent: Dec. 20, 2011

(54) 4-(TETRAZOL-5-YL)-QUINAZOLINE DERIVATIVES AS ANTI-CANCER AGENT

(75) Inventors: Durga Prasad Konakanchi, Hyderabad (IN); Subba Rao Pula, Hyderabad (IN); Lakshmi Ananthaneni, Hyderabad (IN); Muddasani Pulla Reddy, Hyderabad (IN); Bhujanga Rao Adibhatla Kali Satya, Hyderabad (IN); Nannapaneni Venkaiah Chowdary, Hyderabad (IN)

(73) Assignee: Natco Pharma Limited, Hyperabad (IN)

(*) Notice: Subject to any disclaimer, the term of this patent is extended or adjusted under 35 U.S.C. 154(b) by 0 days.

(21) Appl. No.: 12/740,527

(22) PCT Filed: Oct. 28, 2008

(86) PCT No.: PCT/IN2008/000708
§ 371 (c)(1),
(2), (4) Date: Apr. 29, 2010

(87) PCT Pub. No.: WO2009/057139
PCT Pub. Date: May 7, 2009

(65) Prior Publication Data
US 2010/0261740 A1 Oct. 14, 2010

(30) Foreign Application Priority Data
Oct. 29, 2007 (IN) .......................... 2445/CHE/2007

(51) Int. Cl.
*A61K 31/517* (2006.01)
(52) U.S. Cl. .................. 514/266.23; 544/284
(58) Field of Classification Search .................. 544/284
See application file for complete search history.

(56) References Cited

U.S. PATENT DOCUMENTS

| | | | |
|---|---|---|---|
| 3,800,039 A * | 3/1974 | Marquis et al. ............ | 514/266.1 |
| 5,747,498 A | 5/1998 | Schnur et al. | |
| 5,770,599 A | 6/1998 | Gibson | |
| 2004/0048880 A1 | 3/2004 | Himmelsbach et al. | |

FOREIGN PATENT DOCUMENTS

| | | |
|---|---|---|
| EP | 0 211 363 | 2/1987 |
| EP | 0 304 493 | 3/1989 |
| EP | 0 322 738 | 7/1989 |
| EP | 0 400 586 A1 | 12/1990 |
| EP | 0 520 722 A1 | 12/1992 |
| EP | 0 566 226 A1 | 10/1993 |
| EP | 0 602 851 A1 | 6/1994 |
| EP | 0 635 498 A1 | 1/1995 |
| WO | WO 92/20642 | 11/1992 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 97/03069 | 1/1997 |
| WO | WO 97/13771 | 4/1997 |
| WO | WO 97/30034 | 8/1997 |
| WO | WO 97/30035 | 8/1997 |
| WO | WO 97/38983 | 10/1997 |
| WO | WO 98/02434 | 1/1998 |
| WO | WO 98/02437 | 1/1998 |
| WO | WO 98/02438 | 1/1998 |
| WO | WO 98/13354 | 4/1998 |
| WO | WO 99/35132 | 7/1999 |
| WO | WO 99/35146 | 7/1999 |
| WO | WO 01/21596 A1 | 3/2001 |
| WO | WO 01/55141 A1 | 8/2001 |
| WO | WO 01/94341 A1 | 12/2001 |
| WO | WO 02/18372 A1 | 3/2002 |

(Continued)

OTHER PUBLICATIONS

Bokemeyer et al., "Angiotensin II-induced growth of vascular smooth muscle cells requires an Src-dependent activation of the epidermal growth factor receptor," *Kidney International* (2000) 58: 549-558.

Yaish et al., "Locking of EGF-dependent cell proliferation by EGF receptor kinase inhibitors," *Science* (1988) 242 (4880): 933-935.

Toi et al., "Antineoplastic effect of erbstatin on human mammary and esophageal tumors in athymic nude mice," *Eur. J. Cancer* (1990) 16 (6): 722-724.

Yoneda et al., "The antiproliferative effects of tyrosin kinase inhibitors tyrphostins on a human squamous cell carcinoma in Vitro and in nude mice," *Cancer Research* (1991) 51: 4430-4435.

(Continued)

*Primary Examiner* — James O Wilson
*Assistant Examiner* — Brian McDowell
(74) *Attorney, Agent, or Firm* — Merchant & Gould P.C.

(57) ABSTRACT

The invention relates to substituted 4-(tetrazol-5-yl)-quinazoline derivatives of the formula-I,

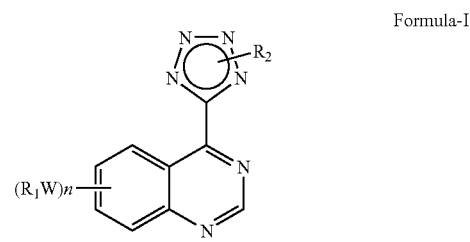

Formula-I or pharmaceutically-acceptable salts thereof, which possess anti-proliferative activity such as anti-cancer activity and are accordingly useful in methods of treatment of the human or animal body. The invention also relates to processes for the manufacture of substituted 4-(tetrazol-5-yl)-quinazoline derivatives, to pharmaceutical compositions containing the compound and to its use in the manufacture of medicaments for the production of an anti-proliferative effect in a warm-blooded animal such as man.

5 Claims, No Drawings

FOREIGN PATENT DOCUMENTS

| | | |
|---|---|---|
| WO | WO 03/040108 A1 | 5/2003 |
| WO | WO 03/040109 A2 | 5/2003 |
| WO | WO 2004/046101 A2 | 3/2004 |
| WO | WO 2004/093880 A1 | 11/2004 |
| WO | WO 2005/051923 A1 | 6/2005 |
| WO | WO 2008/012326 A1 | 1/2008 |

OTHER PUBLICATIONS

Burke, Jr., T.R., "Protein-tyrosine kinase inhibitors," *Drugs of the Future* (1992) 17 (2): 119-131.

Fry et al., "A specific inhibitor of the epidermal growth factor receptor tyrosine kinase," *Science* (1994) 265: 1093-1095.

Mendelsohn et al., "The EGF receptor family as targets for cancer therapy," *Oncogene* (2000) 19: 6550-6565.

Lynch et al., "Activating mutations in the epidermal growth factor receptor underlying responsiveness of non-small-cell lung cancer to gefitnib," *New England Journal of Medicine* (2004) 350: 2129-2139.

Paez et al., "EGFR mutations in lung cancer: correlation with clinical response to gefitinib therapy," *Science* (2004) 304: 1497-1500.

Sordella et al., "Gefitinib-sensitizing EGFR mutations in lung cancer activate anti-apoptotic pathways," *Science* (2004) 305: 1163-1167.

Stephens et al., "Intragenic ERBB2 kinase mutations in tumours," *Nature* (2004) 431: 525-526.

Kant et al., "Preparation and reactions of mono-reissert compounds and analogs at the 3,4-position of quinazoline [1]," *J. Heterocyclic Chem.* (1985) 22: 1313-1316. XP009114027.

Miyashita et al., "Preparation of heteroarenecarbonitriles by reaction of the heteroarene N-oxides with trimethylsilyl cyanide in the presence of DBU," *Heterocycles* (1992) 33 (1): 211-216.

\* cited by examiner

4-(TETRAZOL-5-YL)-QUINAZOLINE DERIVATIVES AS ANTI-CANCER AGENT

This application is a National Stage Application of PCT/IN2008/000708, filed 28 Oct. 2008, which claims benefit of Serial No. 2445/CHE/2007, filed 29 Oct. 2007 in India and which applications are incorporated herein by reference. To the extent appropriate, a claim of priority is made to each of the above disclosed applications.

FIELD OF INVENTION

The invention relates to substituted 4-(tetrazol-5-yl)-quinazoline derivatives of the formula-I,

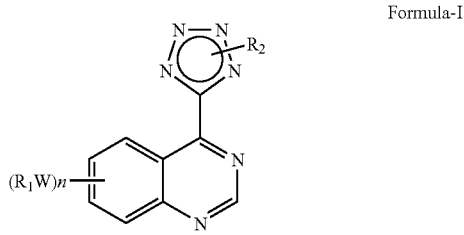

Formula-I or pharmaceutically-acceptable salts thereof, which possess anti-proliferative activity such as anti-cancer activity and are accordingly useful in methods of treatment of the human or animal body. The invention also relates to processes for the manufacture of substituted 4-(tetrazol-5-yl)-quinazoline derivatives, to pharmaceutical compositions containing the compound and to its use in the manufacture of medicaments for the production of an anti-proliferative effect in a warm-blooded animal such as man.

Many of the earlier treatment regimes for cell proliferation diseases such as psoriasis and cancer utilize compounds, which inhibit DNA synthesis. Such compounds are toxic to cells generally but their toxic effect on rapidly dividing cells such as tumour cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, Mutagenesis, 1986, 1, 91). Several such oncogenes give rise to the production of peptides, which are receptors for growth factors. The growth factor receptor complex subsequently leads to an increase in cell proliferation. It is known, for example, that several oncogenes encode tyrosine Kinase enzymes and that certain growth factor receptors are also tyrosine Kinase enzymes (Yarden et al., Ann. Rev. Biochem, 1988, 57, 443; Larsen et al. Ann. Reports in Med. Chem. 1989, Chpt. 13).

Aberrant signal transduction is a hallmark of carcinogenesis. Cell surface receptors, their ligands and protein tyrosine kinases are key components of growth signaling pathways and are mutated or upregulated in a wide variety of human tumors. In particular, the epidermal growth factor receptor (EGFR) pathway has been implicated in tumor-promoting events such as cell division, cell adhesion and migration, angiogenesis, and anti-apoptosis. EGFR overexpression, found in one-third of epithelial cancers overall, can vary from 20 to 80% depending on histologic type and is associated with resistance to hormonal therapy, cytotoxic agents and radiation.

EGFR belongs to the erbB family of structurally related receptors, comprising EGFR (HER-1, erbB1), HER-2/neu (erbB2), HER-3 (erbB3), and HER-4 (erbB4). These transmembrane glycoproteins possess an external ligand-binding domain, a cytoplasmic tyrosine kinase (TK) domain, and a Src homology 2 (SH2) domain for substrate binding. EGF, transforming growth factor-a and amphiregulin bind exclusively to EGFR, while heparin-binding EGF, beta-cellulin and epiregulin bind EGFR and HER-4, and heregulins and neuregulins bind HER-3 and HER-4.

The central role of EGFR in cancer has engendered strenuous efforts to develop EGFR antagonists. The two strategies that are furthest along in clinical trials are receptor monoclonal antibodies, which block ligand binding and receptor activation, and small-molecule inhibitors of EGFR TK. The first-generation small-molecule inhibitors act as ATP analogs competing reversibly for the TK catalytic site. Newer inhibitors that are under development produce irreversible antagonism and/or target multiple erbB receptors Receptor tyrosine kinases are important in the transmission of biochemical signals, which initiate cell replication. They are large enzymes which span the cell membrane and possess an extracellular binding domain for growth factors such as epidermal growth factor (EGF) and an intracellular portion which functions as a Kinase to phosphorylate tyrosine amino acids in proteins and hence to influence cell proliferation. Various classes of receptor tyrosine kinases are known (Wilks, Advances in Cancer Research, 1993, 60, 43-73) based on families of growth factors, which bind to different receptor tyrosine kinases. The classification includes Class I receptor tyrosine kinases comprising the EGF family of receptor tyrosine kinases such as the EGF, TGFα, NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ. and colony stimulating factor 1 (CDF1) receptors.

It is known that Class I kinases such as the EGF family of receptor tyrosine kinases are frequently present in common human cancers such as breast cancer (Sainsbury et. al., Brit J. Cancer, 1988, 58,458; Guerin et al, Oncogene Res., 1988, 3, 21 and Klijn et al., Breast Cancer Res. Treat., 1994, 29, 73), non-small cell lung cancers (NSCLCs) including adenocarcinomas (Cerny et., Brit. J. Cancer, 1986, 54, 265; Reubi et al., Int. J. Cancer, 1990, 45, 269; and Rusch et al., Cancer Research, 1993, 53, 2379) and squamous cell cancer of the lung (Hendler et al., Cancer Cells, 1989, 7, 347), bladder cancer (Neal et al., Lancet, 1985, 366), oesophageal cancer (Mukaida et al., Cancer, 1991, 68, 142), gastrointestinal cancer such as colon, rectal or stomach cancer (Bolen et al., Oncogene Res., 1987, 1, 149), cancer of the prostate (Visakorpi et al., Histochem. J., 1992, 24, 481), leukaemia (Konaka et al., Cell, 1984, 31, 1035) and ovarian, bronchial or pancreatic cancer (European Patent Specification No. 0400586). As further human tumour tissues are tested for the EGF family of receptor tyrosine kinases it is expected that their widespread prevalance will be established in further cancers such as thyroid and uterine cancer. It is also known that EGF type tyrosine Kinase activity is rarely detected in normal cells whereas it is more frequently detectable in malignant cells (Hunter, Cell., 1987, 50, 823). It has been shown more recently (W J Gullick, Brit. Med. Bull., 1991, 47, 87) that EGF receptors which possess tyrosine kinase activity are overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et al. Science, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., Eur. J. Cancer Clin. Oncol., 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al., Cancer Research, 1991, 51, 4430). Various known tyrosine kinase inhibitors are disclosed in a more recent review by T R Burke Jr. (Drugs of the Future, 1992, 17, 119).

It is known from patent Applications Nos EP0520722, EP0566226 and EP0635498 that certain quinazoline derivatives which bear an anilino substituent at the 4-position possess receptor tyrosine kinase inhibitory activity. It is further known from patent Application No. EP0602851 that certain quinazoline derivatives which bear a heteroarylamino substituent at the 4-position also possess receptor tyrosine kinase inhibitory activity.

It is further known from Patent Application No. WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

The in vitro anti-proliferative effect of a 4-anilinoquinazoline derivative has been disclosed by Fry et al., Science, 1994, 265, 1093. It was stated that the compound 4-(3'-bromoanilino)-6,7-dimethoxyquinazoline was a highly potent inhibitor of EGF receptor tyrosine kinase.

It is also expected that inhibitors of EGF type receptor tyrosine kinases will be useful in the treatment of other diseases of excessive cellular proliferation such as psoriasis. AstraZeneca has developed and launched gefitinib (U.S. Pat. No. 5,770,599), of the formula II,

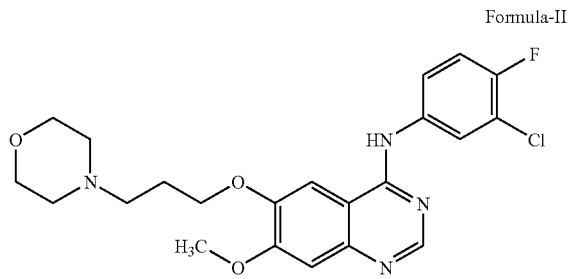

Formula-II an orally active, selective epidermal growth factor receptor-tyrosine kinase inhibitor (EGFR-TK1). It is indicated as monotherapy for the continued treatment of patients with locally advanced or metastatic non-small cell lung cancer after failure of both platinum-based and docetaxel chemotherapies that are benefiting or have benefited from gefitinib. The brand name is Iressa.

OSI Pharmaceuticals has developed and launched Erlotinib (U.S. Pat. No. 5,747,498) of formula-III,

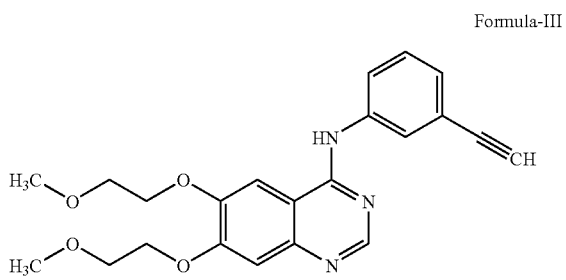

Formula-III an orally active, ATP-competitive small-molecule inhibitor of EGFR TK. It is presently being used as a standard treatment for non-small cell lung cancer (NSCLC) and pancreatic cancer diseases. Its activity is expected to be enhanced when combined with standard cytotoxic antibiotic anti-cancer drugs. The brand name is Tarceva.

Furthermore, inhibitory antibodies against EGFR and erbB2 (Erbitux® (c-225/cetuximab) and Herceptin® (trastuzumab) respectively) have proven to be beneficial in the clinic for the treatment of selected solid tumours (reviewed in Mendelsohn et al, 2000, 5 Oncogene, 19, 6550-6565).

Recently mutations in the ATP binding pocket of the intracellular catalytic domain of the EGF receptor have been discovered in certain sub-sets of non-small cell lung cancers (NSCLCs). The presence of mutations in the receptor appear to correlate with response to EGFR tyrosine kinase inhibitors such as gefitinib (Lynch et al, N Engl J Med 2004; 350: 2129-2139; Paez et al, Science 2004; 304: 1497-1500), although it is becoming evident that the clinical benefits of compounds such as gefitinib and erlotinib are not likely to be mediated by EGFR mutations alone. It has been demonstrated that ligand stimulation results in a different phosphorylation pattern in mutated receptors compared with that seen in wild-type receptors and it is thought that mutant EGF receptors selectively transduce survival signals on which NSCLCs become dependent. Inhibition of those signals by compounds such as gefitinib may contribute to the efficacy of such drugs (Sordella et al. Science 2004; 305: 1163-1167). Similarly, mutations within the erbB2 kinase domain have recently been discovered in certain primary tumours, such as NSCLC, glioblastoma and gastric and ovarian tumours (Stephens et al., Nature 2004; 431; 525-526). Accordingly the inhibition of the EGF and/or erbB2 tyrosine kinase in both wild-type and mutated receptors is an important target that would be expected to provide an anti-cancer effect.

Amplification and/or activity of members of the erbB type receptor tyrosine kinases have been detected and so have been implicated to play a role in a number of non-malignant proliferative disorders such as psoriasis (Ben-Bassat, Curr. Pharm. Pes., 2000, 6, 933; Elder et al., Science, 1989, 243, 811), benign prostatic hyperplasia (BPH) (Kumar et al., Int. Urol. Nephroi., 2000, 32,73), atherosclerosis and restenosis (Bokemeyer et al., Kidney Int., 2000, 58, 549). It is therefore expected that inhibitors of erbB type receptor tyrosine kinases will be useful in the treatment of these and other non-malignant disorders of excessive cellular proliferation WO 96/09294, WO 96/15118, WO 96/16960, WO 96/30347, WO 96/33977, WO96/33978, WO 96/33979, WO 96/33980, WO 96/33981, WO 97/03069, WO 97/13771, WO 97/30034, WO 97/30035, WO 97/38983, WO 98/02437, WO 98/02434, WO 98/02438, WO 98/13354, WO 99/35146, WO 01/21596, WO 01/55141 and WO 02/18372 each disclose that certain quinazoline derivatives which bear an anilino substituent at the 4-position possess receptor tyrosine 1dnase inhibitory activity. WO 99/35132 discloses certain 4-(indazol-5-ylamino)quinazoline derivatives. However, none of these quinazoline derivatives contain a substituent at the 5-position on the quinazoline ring.

WO 01/94341 discloses that certain quinazoline derivatives which carry a 5-substituent are inhibitors of the Src family of non-receptor tyrosine kinases, such as c-Src, c-Yes and c-Fyn. There is no disclosure on WO 01/94341 of 4-(indazol-5-yl amino)quinazoline derivatives wherein the nitrogen atom of the indazolyl group is substituted by a substituent containing an aryl or a heteroaryl group.

WO 03/040108 and WO 03/040109 each disclose that certain quinazoline derivatives which carry a 5-substituent are inhibitors of the erbB family of tyrosine kinase inhibitors, particularly EGF and erbB2 receptor tyrosine kinases. WO 03/040108 and WO 03/040109 each disclose certain 4-(indazol-5-ylamino)quinazoline derivatives. None of the quinazoline derivatives disclosed contain an acyl amino ethoxy group at the 5-position on the quinazoline ring.

US-2004/0048880 discloses certain 4-anilinoquinazoline derivatives and their use in treating tumoural diseases. The quinazoline derivatives do not contain a substituent at the 5-position on the quinazoline ring. WO 2004/46101 discloses certain 4-(indazol-5-ylamino)quinazoline derivatives and their use as inhibitors of EGF and erbB 2 receptor tyrosine kinases. The quinazoline derivatives do not contain a substituent at the 5-position on the quinazoline ring.

WO 2004/093880 and WO 2005/051923 each disclose certain 4-anilinoquinazoline derivatives and their use as inhibitors of erbB2 receptor tyrosine kinase. Neither of these documents disclose a 4-(indazol-5-ylamino)quinazoline derivative.

There remains a need to find further compounds with good in-vivo activity together with improved pharmacological characteristics compared with known erbB tyrosine kinase inhibitors, particularly compounds that are selective erbB2 tyrosine kinase inhibitors. For example, there is a need for novel compounds with advantageous and/or improved characteristics in, but not limited to, for example, (i) physical properties; (ii) favourable DMPK properties, such as high bioavailability and/or advantageous half life and/or advantageous volume of distribution and/or high absorption; (iii) factors that decrease the liability for clinical drug-drug interactions (e.g. cytochrome P450 enzyme inhibition or induction); and (iv) compounds with a reduced liability for QT interval prolongation in patients, for example compounds which are inactive or weakly active in a HERG assay.

Surprisingly, we have now found that a select group of substituted 4-(tetrazol-5-yl)-quinazoline derivatives of the present invention, or a pharmaceutically-acceptable salt thereof, possess potent anti-tumour activity.

Such processes, when used to prepare the quinazoline derivative of the invention, or a pharmaceutically-acceptable salt thereof, are provided as a further feature of the invention and are illustrated by the following representative example. Necessary starting materials may be obtained by standard procedures of organic chemistry. The preparation of such starting materials is described within the accompanying non-limiting Example. Alternatively necessary starting materials are obtainable by analogous procedures to those illustrated, which are within the ordinary skill of an organic chemist.

DETAILED DESCRIPTION OF THE INVENTION

The present invention relates to substituted-4-(tetrazol-5-yl)-quinazoline derivatives of formula-I,

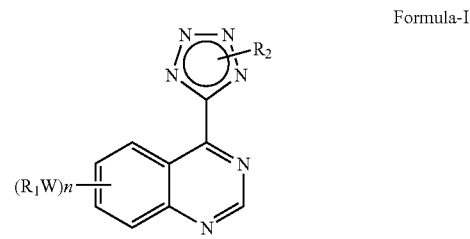

Formula-I where
n is 1, 2, or 3;
W is selected from a single bond, —O—, —S—, —$COR_6$, —NH—, —SO—, —$SO_2$—, —$NR_6CO$—, —$CONR_6$—, —$SO_2NR_7$—, —$NR_7SO_2$—, or —$NR_8$— (wherein $R_6$, $R_7$ and $R_8$ each independently represents hydrogen, $C_1$-$C_6$alkyl, $C_3$-$C_6$cycloalkyl, $C_2$-$C_5$alkenyl, $C_2$-$C_5$alkynyl,
or each $R_1$ is $R_9$ where $R_9$ is independently selected from $C_1$-$C_6$ branched alkyl, $C_2$-$C_6$ branched alkenyl or $C_2$-$C_6$ branched alkynyl;
or each $R_1$ is independently selected from the group consisting of hydrogen, halogen, hydroxy, amino, hydroxylamino, carboxy, nitro, guanidino, ureido, cyano, trifluoromethyl, azido;
or each $R_1$ is independently selected from the group consisting of $C_1$-$C_6$alkyl, $C_3$-$C_6$ cycloalkyl, aryl, heterocyclyl, R3-substituted aryl, R3-substituted heterocyclyl, aryl $C_1$-$C_6$alkoxy, $C_3$-$C_6$cycloalkoxy, ($C_1$-$C_6$)alkanoyloxy, $R_5$-aryloxy, $C_1$-$C_6$alkoxy $C_1$-$C_6$alkyloxy, $C_1$-$C_6$alkoxy-$C_3$-$C_6$cycloalkyloxy, $C_1$-$C_6$alkoxy-$R_5$-aryloxy, $C_1$-$C_6$alkoxy-heterocyclyloxy, $C_1$-$C_6$alkoxy-fused-heterocyclyloxy, N-mono($C_1$-$C_6$)alkylamino, N,N-di($C_1$-$C_6$)alkylamino, formamido, amido, acetamido, $C_1$-$C_6$-alkoxyamino, hydrazino, trifluoromethoxy, alkenyl, alkynyl, aryl, heterocyclyl, fused aryl, fused heteroaryl and . fused heterocyclyl; where $R_3$ is selected from $C_1$-$C_6$ alkyl, $C_3$-$C_6$ cycloalkyl, aryl, and aralkyl; $R_5$ is independently hydrogen or $R_4$; and where $R_4$ is $C_1$-$C_4$ alkyl;
or each $R_1$ is independently selected from $R_9$-substituted by halogen, hydroxy, amino, hydroxylamino, carboxy, nitro, guanidino, ureido, cyano, trifluoromethyl, azido;
wherein $R_9$ is selected from the group consisting of $R_4$, —$OR_5$, —$NR_5R_5$, —$C(O)R_6$, —$NHOR_4$, —$OC(O)R_5$, P and -$QR_4$; $R_6$ is $R_3$, —$OR_5$ or —$NR_5R_5$; P is selected from piperidino, morpholino, pyrrolidino, 4-$R_3$-piperazin-1-yl, imidazol-1-yl, 4-pyridon-1-yl, —($C_1$-$C_4$alkylene)($CO_2H$), phenoxy, phenyl, phenylsulfonyl, $C_2$-$C_4$alkenyl, and —($C_1$-$C_4$alkylene)$C(O)NR_5R_5$; and Q is S, SO, or $SO_2$;
or each $R_1$ is independently selected from phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R_4$—($C_2$-$C_4$)-alkanoylamino and wherein said —$NHSO_2R_4$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R_4$—($C_2$-$C_4$)-alkanoylamino $R_1$ groups are optionally substituted by 1 or 2 substituents independently selected from halo, $C_1$-$C_4$alkyl, cyano, methanesulfonyl and $C_1$-$C_4$alkoxy;
$R_2$ is hydrogen or selected from the group consisting of $C_1$-$C_6$alkyl, $C_3$-$C_6$cycloalkyl, ($C_1$-$C_6$)carbonyloxyalkyl, $R_4$-aryl, $R_4$-aryl substituted with $(R_{11})m$, where $m=1$, 2 or 3 and $R_{11}$ is independently selected from the group consisting of hydrogen, halogen, hydroxy, hydroxylamino, carboxy, nitro, guanidino, ureido, cyano, trifluoromethyl, azido, or $R_3$ (as defined above), $R_4$-fused aryl, $R_4$-fused aryl substituted with $(R_{10})m$, $R_4$-heterocyclyl, $R_4$-heterocyclyl substituted with $(R_{11})m$, $R_4$-fused heterocyclyl, $R_4$-fused heterocyclyl substituted with $(R_{11})m$. $R_4$—$C_1$-$C_6$alkyloxy, $R_4$—$C_1$-$C_6$alkyloxy substituted with $(R_{11})m$, $R_4$—$C_3$-$C_6$cycloalkyloxy, $R_4$—$C_3$-$C_6$cycloalkyloxy substituted with $(R_{11})m$, $C_1$-$C_6$alkoxy-$R_5$-aryloxy, $C_1$-$C_6$alkoxy-$R_5$-aryloxy substituted with $(R_{11})m$, $C_1$-$C_6$alkoxy hetero-cyclyloxy, $C_1$-$C_6$alkoxy-heterocyclyloxy substituted with $(R_{11})m$, $C_1$-$C_6$alkoxy fused heterocyclyloxy, $C_1$-$C_6$alkoxy fused heterocyclyloxy substituted with $(R_{11})m$, N-mono($C_1$-$C_6$)alkylamino, N-mono($C_1$-$C_6$)alkylamino substituted with $(R_{11})m$, N,N-di($C_1$-$C_6$)alkylamino, N,N-di($C_1$-$C_6$)alkylamino substituted with $(R_{11})m$, formamido, amido, acetamido, $C_1$-$C_6$alkoxyamino, hydrazino, trifluoromethoxy, $C_2$-$C_6$alkenyl, $C_2$-$C_6$alkenyl substituted with $(R_{11})m$, $C_2$-$C_6$alkynyl, $C_2$-$C_6$alkynyl substituted with $(R_{11})m$.

DETAILED DESCRIPTION OF THE INVENTION

Formula-I compounds and pharmaceutically acceptable salts thereof may be prepared by any process known to be applicable to the chemically related compounds. In general the active compounds may be made from the appropriate substituted 4-halo quinazoline compounds derived from the predecessors substituted 4H-quinazolin-4-ones. The active compounds of present invention are prepared by the following synthetic Scheme-I.

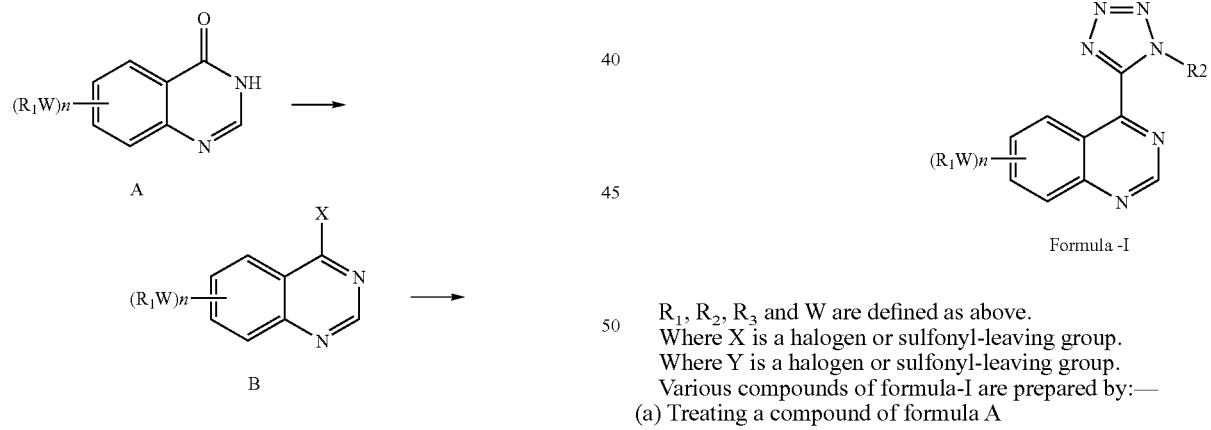

$R_1$, $R_2$, $R_3$ and W are defined as above.
Where X is a halogen or sulfonyl-leaving group.
Where Y is a halogen or sulfonyl-leaving group.
Various compounds of formula-I are prepared by:—
(a) Treating a compound of formula A

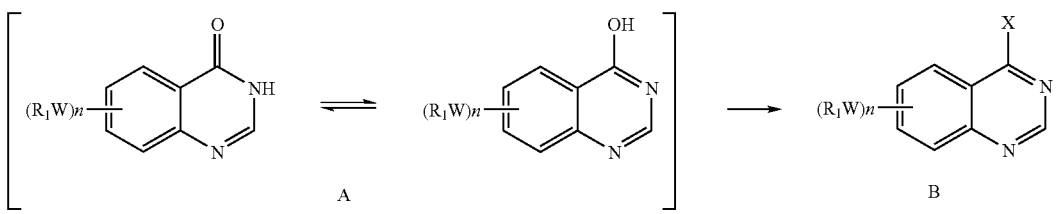

with a halogenating agent such as thionyl halide, phosphorus trihalide, phosphorus pentahalide, phosphoryl trihalide to obtain 4-halo substituted quinazoline derivatves of formula-B, wherein $R_1$, W and n are as defined above. The reaction can be performed either neatly without any solvent or with solvents such as methylene chloride, ethylene dichloride, toluene, xylene, cyclohexane, etc. The temperature of the reaction. is maintained between 25° C. to 150° C., preferably the reflux temperature of halogenating reagent.

(b) Treating the compound of formula-B,

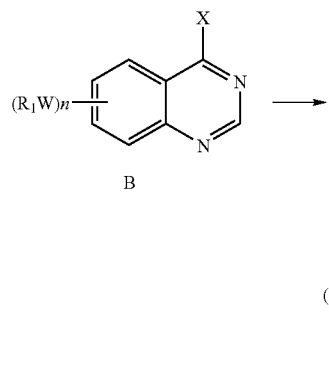

with trialkyl amine ($NR_3$) (where $R_3$ is defined as above) in a suitable solvent such as toluene, xylene, cyclohexane or $C_1$-$C_6$ linear or branched alkenes to obtain the substituted quinazolinyl-4-trialkylamine halide quaternary salts. The temperature of the reaction is maintained between 25° C. to 150° C., preferably the room temperature conditions.

(c) Treating the compound of formula-C,

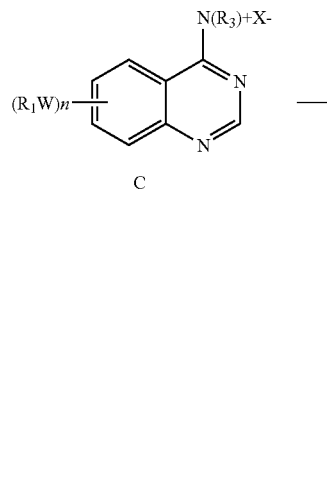

with cyanating agents such as sodium cyanide, potassium cyanide, cuprous cyanide, trialkyl silyl cyanide etc., in a suitable solvent such as toluene, xylene, cyclohexane or $C_1$-$C_6$ linear or branched alkenes, dimethylformamide, dimethylacetamide, formamide, etc., to obtain the substituted 4-amino quinazolines of formula-D, where $R_1$ and n are as defined above. The temperature of the reaction is maintained between 25° C. to 150° C., preferably at 100° C. -125° C.

(d) Treating the compound of formula-D,

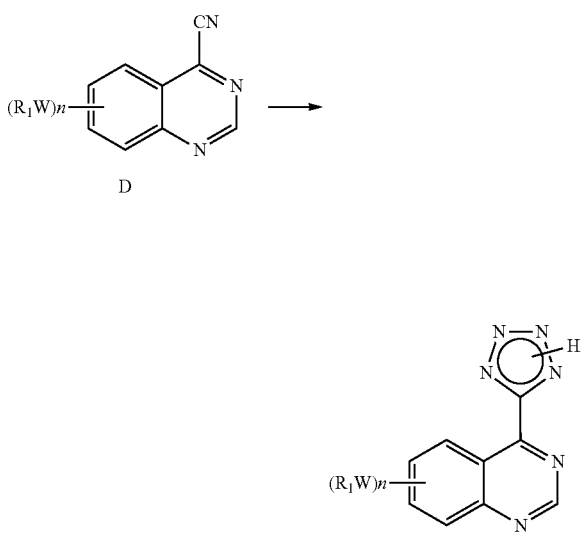

with azidating agents such as sodium azide, trialkyl silylazide, etc., to obtain the compounds of formula E where $R_1$ and n are as defined above.

The reaction is preferably carried out in the presence of a suitable solvent or diluent, for example an alkanol such as methanol, ethanol, isopropanol, an ester solvent such as ethyl acetate, a halogenated solvent such as methylene chloride, chloroform or carbon tetrachloride, an ether solvent such as tetrahydrofuran, 1,4-dioxane, an aromatic hydrocarbon solvent such as toluene, or a dipolar aprotic solvent such as N,N-dimethylformamide, N,N-dimethylacetamide, N-methylpyrrolidin-2-one or dimethyl sulphoxide.

The reaction is conveniently carried out at a temperature in the range, for example, 10-150° C., preferably in the range 50-120° C.

(e) Treating the compound of formula-E,

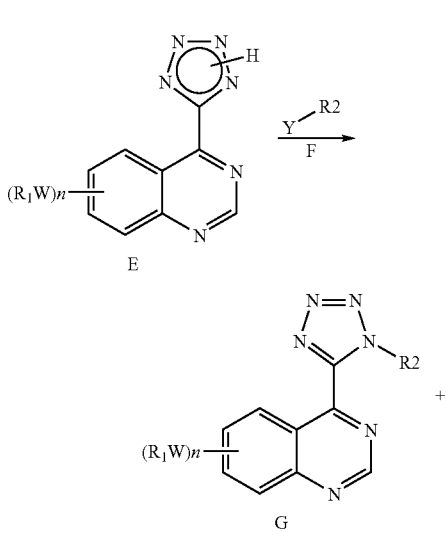

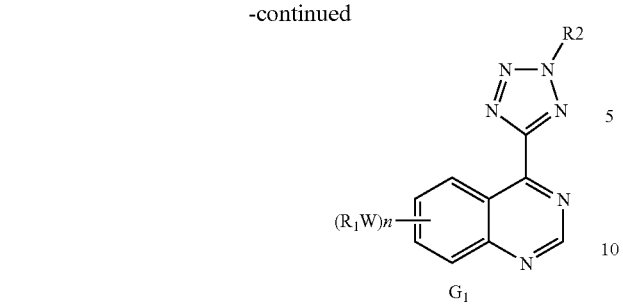

with alkylating agents of formula F (Y and R₂, as defined above) using a base such as alkaline metal carbonates, hydroxides, metal hydrides, metal alkoxides, tetra-alkyl guanidines, alkyl lithium, LDA, etc. The solvents used are acetonitrile, dimethyl-formamide, dimethylacetamide, tetrahydrofuran, toluene, etc. The reaction is conveniently carried out at a temperature in the range, for example, 10-150° C., preferably in the range 20-80° C.

(f) Purifying the compound mixture of formula-G (and its isomer G₁),

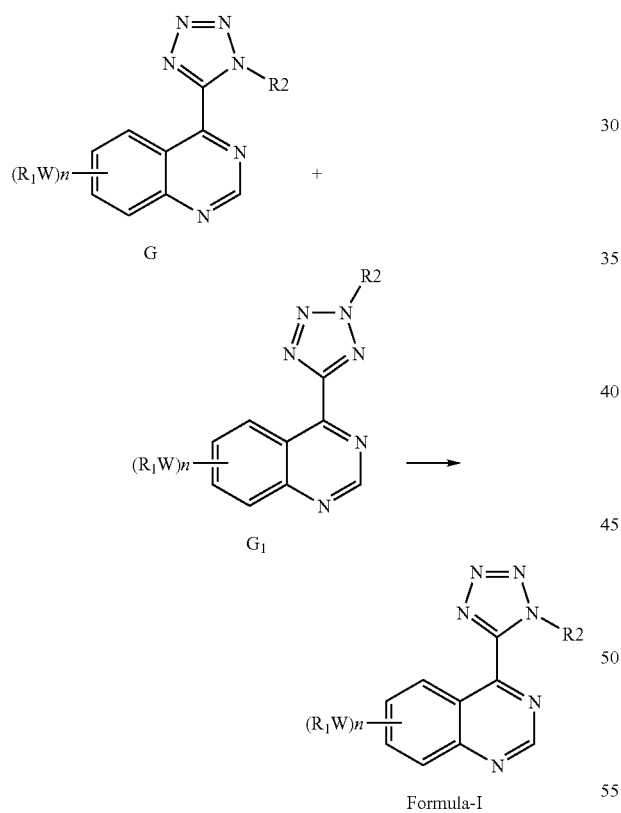

by recrystallisation from a suitable solvent or by preparative chromatography to obtain the required 1H-tetrazolyl derivative.

Compounds of formula-I with substitutions on 6,7-positions with oxygen linkage and their pharmaceutically acceptable salts there of may be prepared by any process known to be applicable to the chemically related compounds. In general the active compounds may be made from the appropriate substituted 4-chloro-6,7-O-protected quinazoline compounds derived from the predecessors, substituted 4H-quinazolin-4-ones. The active compounds of formula-I are prepared by the following synthetic scheme-II.

Scheme-II

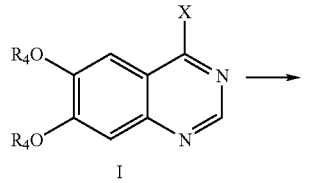

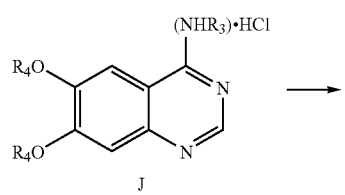

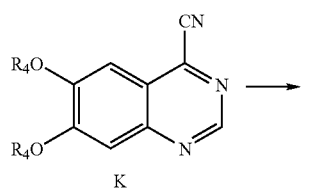

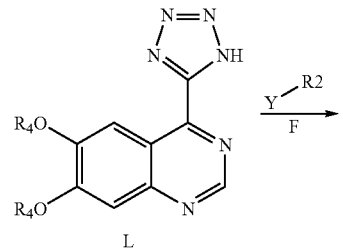

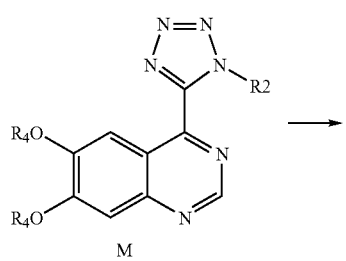

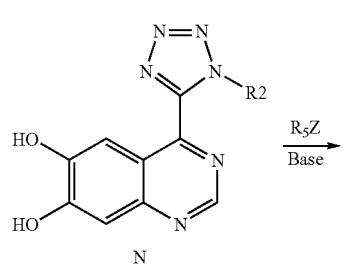

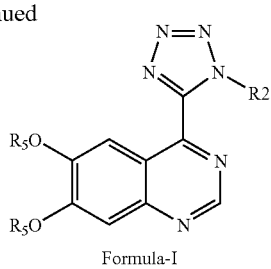

Formula-I

Wherein $R_4$ and $R_5$ are defined as above and Y is a suitable protecting group and such as acyl, benzyl, benzoyl, silyl, alkylsulfonyl, arylsulfonyl, arlkylsulfonyl, etc.; Z is halo or a suitable sulfone containing leaving group.

The base used in the O-alkylation step is taken from alkali carbonates, alkali hydroxides, metallic alkoxides, alkali hydrides, alkyl lithium, tetramethyl guanidine etc.

(a) Treating a compound of formula H (or its tautomer of formula $H_1$)

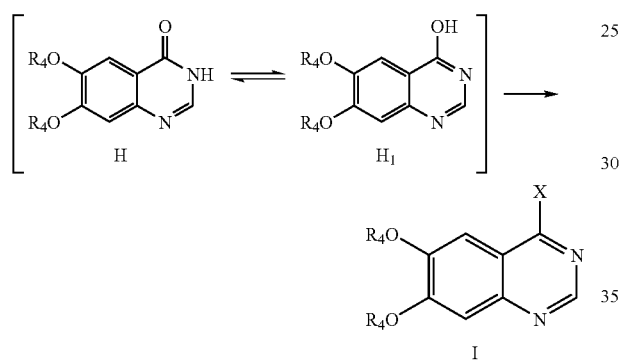

with a halogenating agent such as thionyl halide, phosphorus trihalide, phosphorus pentahalide, phosphoryl trihalide to obtain 4-halo substituted quinazoline derivatives of formula-B, wherein $R_4$ and X are as defined above. The reaction is tried either neatly without any solvent or with solvents such as methylene chloride, ethylene dichloride, toluene, xylene, cyclohexane, etc. The temperature of the reaction is maintained between 25° C.-150° C., preferably the reflux temperature of halogenating agent.

(b) Treating the compound of formula-I

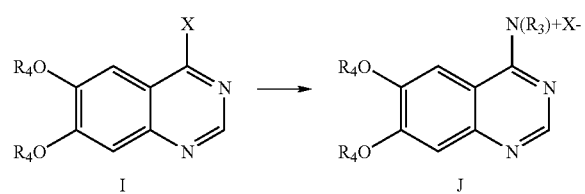

with trialkyl amine ($NR_3$, where $R_3$ is defined as above). The reaction is carried out in a suitable solvent such as toluene, xylene, cyclohexane or $C_1$-$C_6$ linear or branched alkenes to obtain the substituted quinazolin-4-yl-quaternary trialkylamine halide salts. The temperature of the reaction is maintained between 25° C. to 150° C., preferably under the room temperature conditions.

(c) Treating the compound of formula-J,

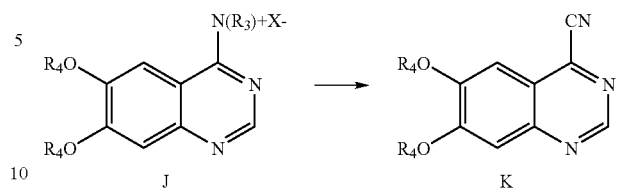

with cyanating agents such as sodium cyanide, potassium cyanide, cuprous cyanide, trialkyl silyl cyanide etc., in a suitable solvent such as toluene, xylene, cyclohexane or $C_1$-$C_6$ linear or branched alkenes, dimethylformamide, dimethylacetamide, formamide, etc., to obtain the substituted 4-cyanoquinazolines of formula-K, where $R_3$, $R_4$ and X are defined as above. The temperature of the reaction is maintained between 25° C. to 150° C., preferably at 100° C. -125° C.

(d) Treating the compound of form

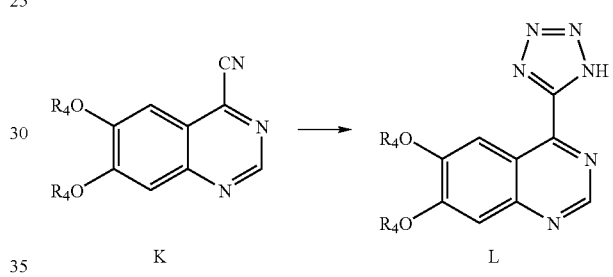

with azidating agents such sodium azide, potassium azide, trialkyl silyl azide, etc.

The reaction is preferably carried out in the presence of a suitable solvent or diluent, for example an alkanol such as methanol, ethanol, isopropanol or ester such as ethyl acetate, a halogenated solvent such as methylene chloride, chloroform or carbon tetrachloride, an ether solvent such as tetrahydrofuran or 1,4-dioxane, an aromatic hydrocarbon solvent such as toluene, or a dipolar aprotic solvent such as N,N-dimethylformamide, N,N-dimethylacetamide, N-methylpyrrolidin-2-one or dimethyl sulphoxide.

The reaction is conveniently carried out at a temperature in the range, for example, 10 to 150.degree. C., preferably in the range 50 to 120.degree. C.

(e) Treating the compound of formula-L,

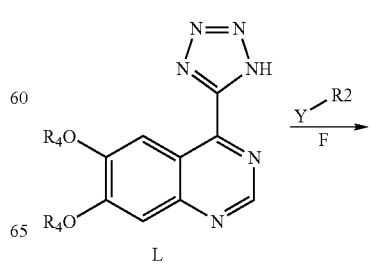

-continued

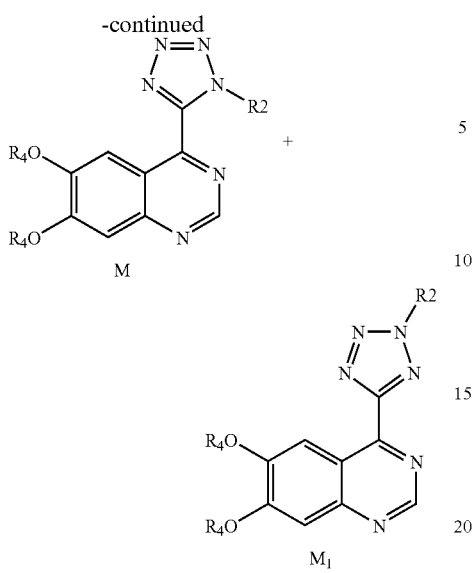

with alkylating agents of compounds of formula F (Y and $R_2$, as defined above) using a base such as alkaline metal carbonates, hydroxides, hydrides, tetra-alkyl guanidines, alkyl lithium, LDA, etc. The solvents used are acetonitrile, dimethylformamaide, dimethyl acetamide, tetrahydrofuran, toluene, etc. The reaction is conveniently carried out at a temperature in the range, for example, 10-150° C., preferably in the range of 20-80° C.

(f) Purifying the compound mixture of formula-M (and its isomer M1),

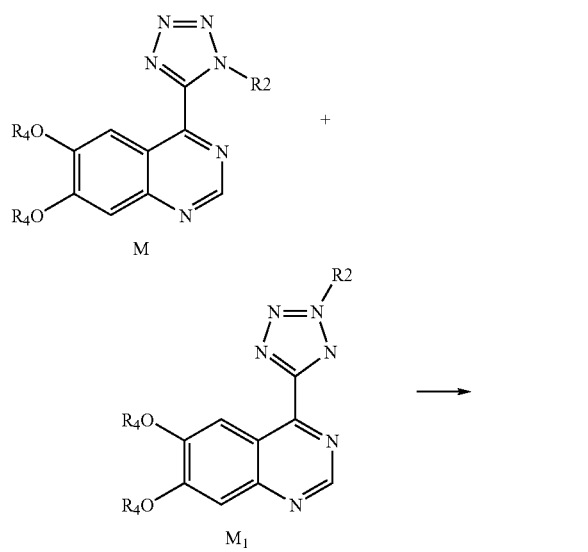

by recrystallisation from a suitable solvent or by preparative chromatography to obtain 1H tetrazolyl derivative of formula-N

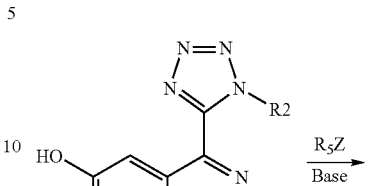

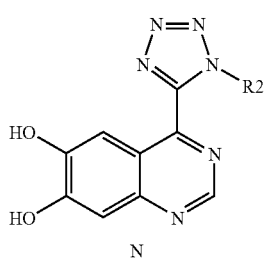

(g) reaction of compounds of formula-N with alkylating agents of formula-$R_5Z$ (where Z and $R_5$ are as defined above), using a base such as alkaline metal carbonates, hydroxides, metal hydrides, tetra-alkyl guanidines, alkyl lithium, LDA, etc. The solvents used are acetonitrile, dimethylformamaide, dimethyl acetamide, tetrahydrofuran, toluene, etc. The reaction is conveniently carried out at a temperature in the range of, for example, 10-150° C., preferably in the range of 20-80° C.

It is also to be understood that certain quinazoline derivatives of the formula I can exist in solvated as well as unsolvated forms such as, for example, hydrated forms. It is to be understood that the invention encompasses all such solvated forms, which possess anti-proliferative activity.

A suitable pharmaceutically acceptable salt of the quinazoline derivative of the invention is, for example, a mono- or di-acid-addition salt of the quinazoline derivative of the invention which is sufficiently basic, for example, an acid-addition salt with, for example, an inorganic or organic acid, for example, hydrochloric, hydrobromic, sulphuric, phosphoric, trifluoroacetic, citric, maleic, tartaric, fumaric, methanesulphonic, or 4-toluenesulphonic acid.

The invention most particularly relates to novel intermediate compounds of the formula I selected from the group consisting of 6,7-Dimethoxy substituted 4-(tetrazoly-5-yl)quinazoline derivatives of formula-IV to VII

5

| Compound Number | Structure | Chemical name |
| --- | --- | --- |
| IV | 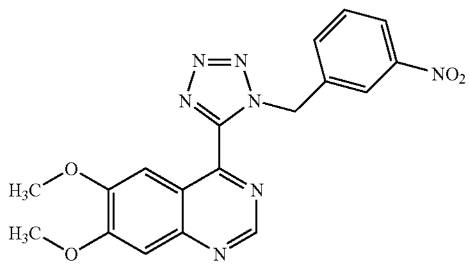 | 6,7-Dimethoxy-4-(1-(3-nitrobenzyl)-1H-tetrazol-5-yl)quinazoline |
| V | 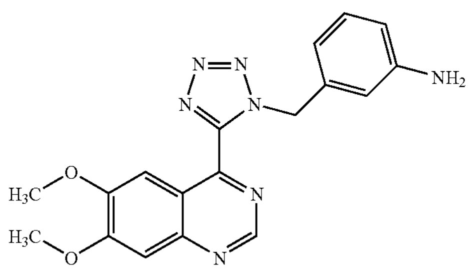 | 6,7-Dimethoxy-4-(1-(3-aminobenzyl)-1H-tetrazol-5-yl)quinazoline |
| VI | 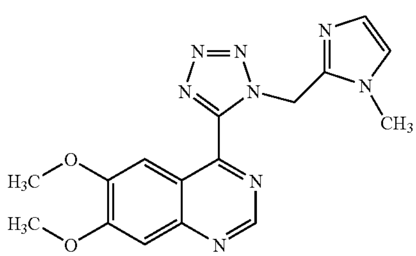 | 6,7-dimethoxy-4-(1-((1-methyl-1H-imidazol-2-yl)methyl)-1H-tetrazol-5-yl)quinazoline |
| VII | | 6,7-dimethoxy-4-(1-(pyridin-2-ylmethyl)-1H-tetrazol-5-yl)-quinazoline | i) 6,7-Dimethoxy quinazoline derivatives

| Compound Number | Structure | Chemical name |
|---|---|---|
| IV b | 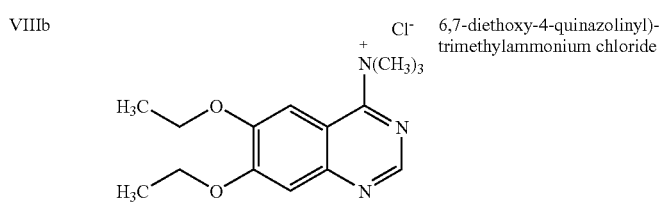 | 6,7-dimethoxy-4-quinazolinyl)-trimethylammonium chloride |
| IV d | 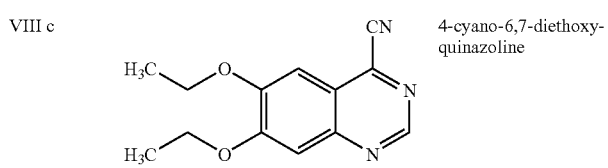 | 6,7-dimethoxy-4-(1H-tetrazol-5-yl) quinazoline | ii) 6,7-Diethoxy quinazoline derivatives

| Compound Number | Structure | Chemical name |
|---|---|---|
| VIII a | 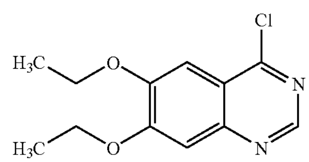 | 4-chloro-6,7-diethoxy-quinazoline |
| VIIIb | 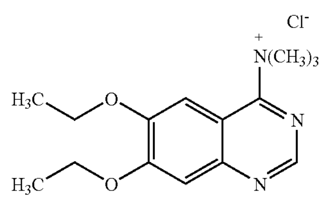 | 6,7-diethoxy-4-quinazolinyl)-trimethylammonium chloride |
| VIII c | 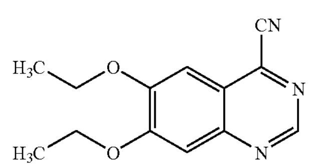 | 4-cyano-6,7-diethoxy-quinazoline |
| VIII d | 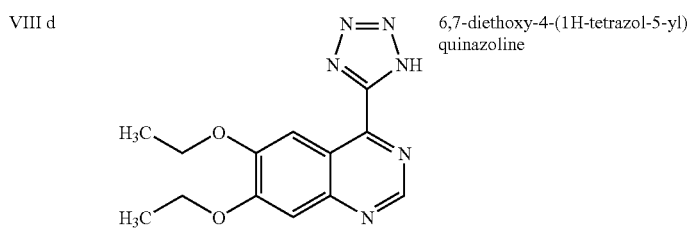 | 6,7-diethoxy-4-(1H-tetrazol-5-yl) quinazoline | iii) 6,7-Di-n-propoxy quinazoline derivatives

| Compound Number | Structure | Chemical name |
|---|---|---|
| XII a | 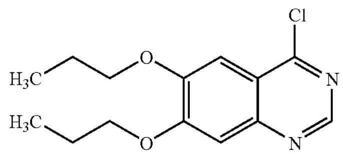 | 4-chloro-6,7-dipropoxy-quinazoline |
| XII b | 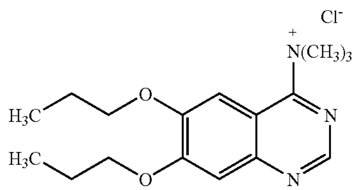 | 6,7-dipropoxy-4-quinazolinyl)-trimethylammonium chloride |
| XII c | 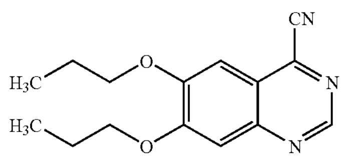 | 4-cyano-6,7-dipropoxy-quinazoline |
| XII d | | 6,7-dipropoxy-4-(1H-tetrazol-5-yl) quinazoline | iv) 6,7-Diethoxy substituted 4-(tetrazoly-5-yl)quinazoline derivatives of formula-VIII to

| Compound Number | Structure | Chemical name |
|---|---|---|
| VIII | 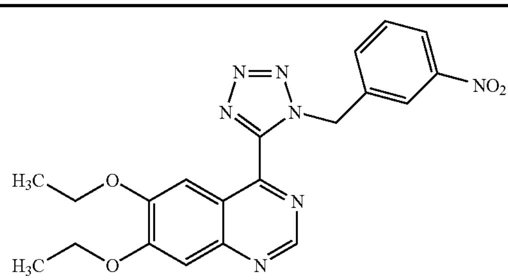 | 6,7-Diethoxy-4-(1-(3-nitrobenzyl)-1H-tetrazol-5-yl) quinazoline |
| IX | 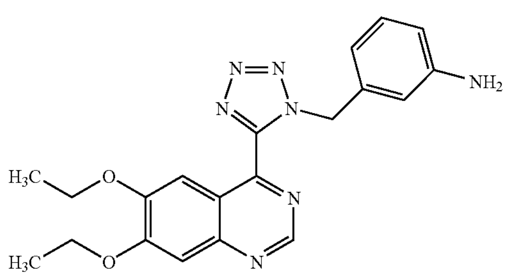 | 3-((5-(6,7-diethoxyquinazolin-4-yl)-1H-tetrazol-1-yl) methyl) aniline |

-continued

| Compound Number | Structure | Chemical name |
|---|---|---|
| X | 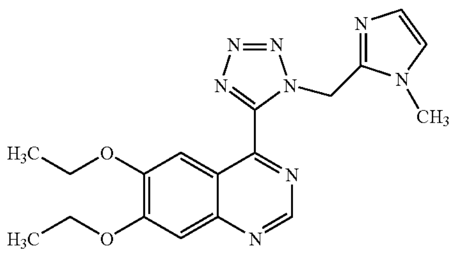 | 6,7-diethoxy-4-(1-((1-methyl-1H-imidazol-2-yl) methyl)-1H-tetrazol-5-yl) quinazoline |
| XI | 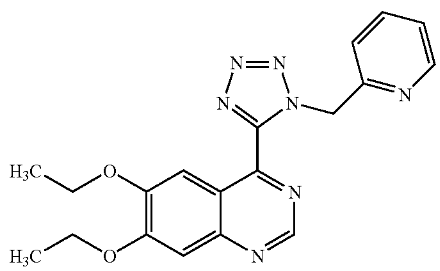 | 6,7-diethoxy-4-(1-(pyridin-2-ylmethyl)-1H-tetrazol-5-yl)quinazoline |

XI v) 6,7-Di-n-propoxy substituted 4-(tetrazoly-5-yl)quinazoline derivatives of formula-XII to XV.

| Compound Number | Structure | Chemical name |
|---|---|---|
| XII | 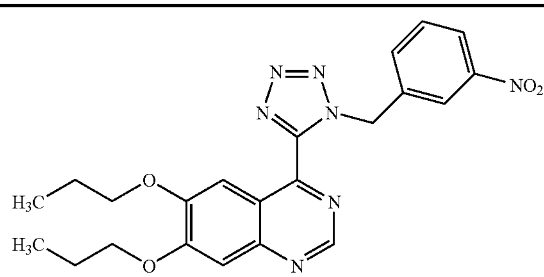 | 6,7-Di-n-propoxy-4-(1-(3-nitrobenzyl)-1H-tetrazol-5-yl)quinazoline |
| XIII | 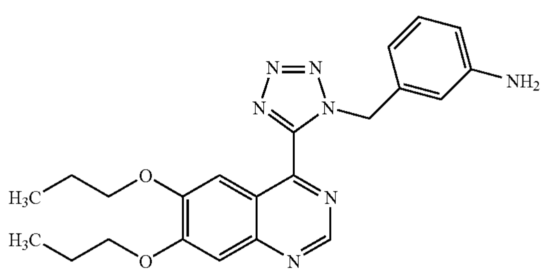 | 3-((5-(6,7-Di-n-propoxyquinazolin-4-yl)-1H-tetrazol-1-yl)methyl)aniline |
| XIV | 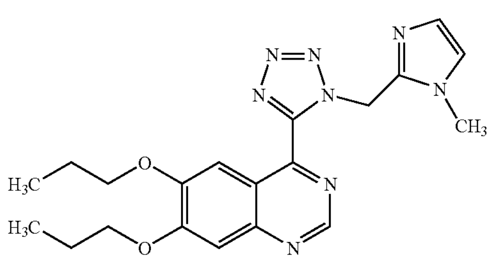 | 4-(1-((1-methyl-1H-imidazol-2-yl) methyl)-1H-tetrazol-5-yl)-6,7-di-n-propoxyquinazoline |

| Compound Number | Structure | Chemical name |
|---|---|---|
| XV | 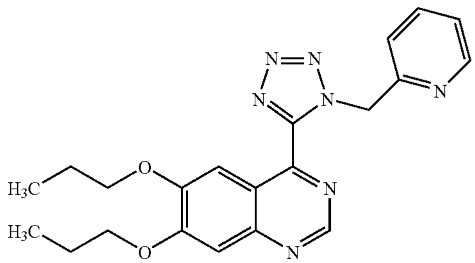 | 6,7-Di-n-propoxy-4-(1-(pyridin-2-ylmethyl)-1H-tetrazol-5-yl)quinazoline |

Within the present invention it is to be understood that, insofar as certain of the compounds of the formula I may exist in optically active or racemic forms by virtue of one or more substituents containing an asymmetric carbon atom, the invention encompasses any such optically active or racemic form which possesses anti-proliferative activity. The synthesis of optically active forms may be carried out by standard techniques of organic chemistry well known in the art, for example by synthesis from optically active starting materials or by resolution of a racemic form.

In Vitro Studies

MTT Proliferation Assay

MTT [3-(4,5-dimethylthiazol-2-yl)-2,5-diphenyltetrazolium bromide] assay, first described by Mosmann in 1983, is based on the ability of a mitochondrial dehydrogenase enzyme from viable cells to cleave the tetrazolium rings of the pale yellow MTT and form dark blue formazan crystals largely impermeable to cell membranes, thus resulting in its accumulation within healthy cells. Solubilization of the cells by the addition of a detergent results in the liberation of the crystals, which are solubilized. The number of surviving cells is directly proportional to the level of the formazan product created. The color can then be quantified using a simple colorimetric assay. This assay was done using 0-1000 ng/ml concentrations of Erlotinib and its derivatives in A549 and H1299 cells. The protocol was based on ATCC and as per manufacturers instructions (Catalog Number 30-1010K).

Western Blot Analysis

Ideal drug concentrations determined from the MTT proliferation assay were used to treat $1 \times 10_6$ A549 or H1299 cells in appropriate media for 72 h following which cell lysates were extracted and fractionated on a 10% SDS PAGE gel under reducing conditions. The gels were blotted onto treated nylon membranes (Bio-Rad) and immunoprobed for EGFR, PI3K and AKT.

Matrigel Invasion Assay

The in vitro invasiveness of H1299 or A549 cells in the presence of various concentrations of NRC compounds (as determined by MTT assay) was assessed using a modified Boyden chamber assay. Cells were treated with these compounds for 48 h. $1 \times 10_6$ cells were suspended in 600 μl of serum-free medium supplemented with 0.2% BSA and placed in the upper compartment of the transwell chambers (Corning Costar Fischer Scientific Cat #07-200-158, Pittsburgh Pa.) coated with Matrigel (0.7 mg/ml). The lower compartment of the chamber was filled with 200 μl of serum-medium and the cells were allowed to migrate for 24 h. After incubation, the cells were fixed and stained with Hema-3 and quantified as previously described (Mohanam, et al. 1993). The migrated cells were quantified as percent invasion.

In Vitro Angiogenic Assay

To determine the anti-angiogenic properties of Erlotinib and its derivatives, ideal concentration of drugs were used to treat A549 cells for 72 h as described earlier, after which, complete media was replaced with serum-free media for 12 h. This serum-free media was termed as conditioned media and used for angiogenic induction on HMEC cells grown to 80% confluency as per standard protocols.

Western Blot Analysis

As described previously, ideal drug concentrations determined from the MTT proliferation assay were used to treat $1 \times 10_6$ A549 or H1299 cells in appropriate media for 72 h followed by western blotting. Using A549 cells the above mentioned compounds induced a dose dependent decrease in EGFR expression levels. H1299 cells showed a similar decrease in EGFR expression levels when treated with above mentioned compounds, but were less responsive than A549 cells.

Matrigel Invasion Assay

Matrigel invasion was performed as described in materials and methods. Using A549 cells the control compound Erlotinib decreased invasiveness in a dose dependent manner from 100 to 800 ng/ml. The above mentioned compounds caused retardation of invasion similar to Erlotinib at $\frac{1}{10}_{th}$ concentration (10-80 ng/ml). Using H1299 cells similar retardation patterns of invasion was observed.

In Vivo Studies:

Effect of the Above Mentioned Compounds on Subcutaneous Lung Tumors in Nude Mice Method Nude mice were implanted with $2 \times 10_6$ A549 cells in the right hind limb flank. Upon the observance of a tumor (>2 mm), mice were given oral or ip treatments of Erlotinib, and above-mentioned compounds at $\frac{1}{10}^{th}$ of dose of Erlotinib. From a literature search, 100 mg/kg of Erlotinib had been identified as the base line dose. The above mentioned compounds caused retardation of tumor growth similar to Erlotinib at ¹/₁₀th concentration (10-80 ng/ml).

ADVANTAGES OF PRESENT INVENTION

1. The above-mentioned novel compounds are superior to the existing standard therapies of non-small cell lung cancers such as Gefitinib and Erlotinib and are potentially useful in lung cancer therapy.

2. The above-mentioned novel compounds are also working on other area such as pancreatic cancer and are potentially useful in pancreatic-cancer therapy.

3. The above-mentioned novel compounds are also working on other area such as throat and oral cancer and are potentially useful in throat and oral cancer therapy.

The invention will be more fully described in conjunction with the following specific examples, which are not to be construed as limiting the scope of the invention.

EXPERIMENTAL PROCEDURE

Example-1

1a) Preparation of 4-chloro-6,7-dimethoxy-quinazoline

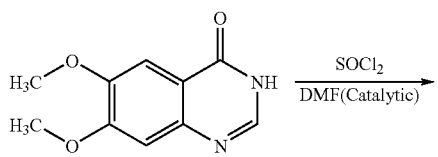

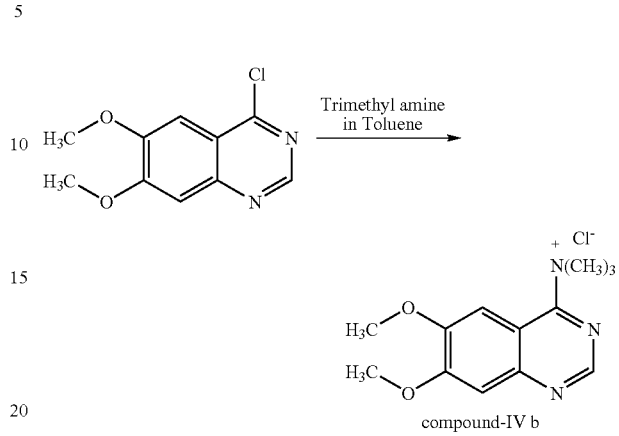

compound-IVa 720.0 g (6.05 mol) of thionyl chloride and 50.0 g (0.243 mol) of 6,7-dimethoxy-3H-quinazoline-4-one were charged into a 2.0 L 4 necked round bottom flask connected to a mechanical stirrer, thermometer socket and double surface reflux condenser. Reaction mass temperature was raised to reflux temperature (78-80° C.). 20.0 ml of dimethyl formamide was added slowly at reflux temperature. Maintained the mass temperature at reflux for 7-8 hours under stirring. Distilled off thionyl chloride completely under vacuum at below 70° C. Cooled the mass temperature to 40° C. to 45° C. under nitrogen atmosphere 1000.0 ml of hexane was charged under stirring. Maintained the mass temperature at 40° C. to 45° C. for 30-45 min. Cooled the mass temperature 25-30° C. Maintained the mass temperature at 25-30° C. for 45-60 min under nitrogen atmosphere. Filtered the solid under nitrogen atmosphere. Solid was washed with 250.0 ml of hexane. Compound was dried in vacuum tray drier containing phosphorus pentoxide at 30-35° C. till the loss on drying is not more than 0.50% w/w. Obtained 52.50 g (yield is 96.33% by theory) of yellow coloured product.

Melting range 214-220° C.

HPLC purity 96.5%.

Spectral data: FT-IR (KBr): 3060, 3041, 2951, 2838, 1618, 1562, 1505, 1429, 1360, 1336, 1232, 1163, 966, 878, 853, 806, 656, 615, 493, 471.

$^1$HNMR (DMSO-$d_6$): δ Value (ppm): 3.89-3.91 (m) 2(O—CH3)(6H), 7.37 (s) Ar-Ha (1H), 7.46 (s) Ar-Hb91H), 9.01 (s) Hc (1H).

$^{13}$CNMR: δ value (ppm): 56.55 (2C), 101.69 (1C), 105.95 (1C), 113.39 (1C), 134.28 (1C), 148.01 (1C), 150.15 (1C), 155.68 (1C), 157.30 (1C), 157.80 (1C)

Mass: 225.6 [M+1], 224.6 [M]

1b) Preparation of 6,7-dimethoxy-4-quinazolinyl)-trimethylammonium chloride

Experimental Procedure: 6.50 Lt's of trimethylamine in toluene solution was taken into a 10.0 L 4 necked round bottom flask connected to a mechanical stirrer, thermometer socket and condenser. Cooled the mass to 15-20° C. 50.0 g (0.22 mol) of 4-chloro-6,7-dimethoxy-quinazoline was charged under stirring at 15-20° C. Stirred the mass for 60-90 min at 15-20° C. Insoluble compound was filtered and filtrate was collected into a 10.0 L 4 necked round bottom flask. Closed the flask with stoppers. Solution was stored at 25-35° C. for 7 days without stirring. Filtered the solid and solid was washed with 100.0 ml of toluene under nitrogen atmosphere. Compound was dried in vacuum tray drier containing phosphorus pentoxide at 30-35° C. till the loss on drying is not more than 1.0% w/w. Obtained 38.80 g(yield is 61.45% by theory) of light yellow coloured product.

Melting range 218-224° C.

HPLC purity 94.8%.

Spectral data: FT-IR (KBr): 3416, 3027, 1615, 1509, 1479, 1447, 1413, 1361, 1350, 1276, 1239, 1205, 1168, 975, 884, 830, 662, 572.

$^1$H NMR (DMSO-$d_6$): δ Value (ppm): 2.27 (s) N—(CH3)$_3$ (9H), 3.83 (s) 2(O—CH3) (6H), 7.24 (s) Ar-Ha (1H), 7.41 (s) Ar-Hb (1H), 8.49 (Hc) (1H).

$^{13}$CNMR δ value (ppm): 51.1 (3C), 56.1 (2C), 103.5 (1C), 108.9 (1C), 119.2 (1C), 148.1 (1C), 152.3 (1C), 154.9 (1C), 159.2 (1C), 178.1 (1C)

Mass: 284.5 [M+1], 283.4 [M]

1c) Preparation of 4-cyano-6,7-dimethoxy-quinazoline

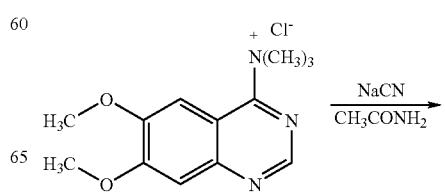

29
-continued

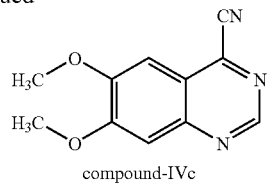
compound-IVc

Experimental Procedure: 1800.0 ml of toluene and 37.0 g (0.13 mol) of 6,7-dimethoxy-4-quinazolinyl)-trimethylammonium chloride were charged into a 3.0 L 4 necked round bottom flask, connected to a mechanical stirrer, thermometer socket, condenser, and dean-stark apparatus. Raised the mass temperature under azeotropic conditions to reflux temperature. Maintained the mass temperature at reflux till theoretical quantity of water is separated. After water separation was completed, distilled 400.0 ml toluene. Cooled the mass temperature to 95-100° C. 46.0 g (0.78 mol) of acetamide was charged at 95-100° C. Maintained the mass temperature at 95-100° C. for 20-30 min. 19.80 g (0.40 mol) of sodium cyanide was charged at 95-100° C. Maintained the mass temperature at 95-100° C. for 20-30 min. Reaction mass temperature was raised to reflux temperature under azeotropic conditions. Maintained the mass temperature at reflux till the completion of water separation by azetropically. After water separation was completed, cooled the mass temperature to 95-100° C. Maintained the mass temperature at 90-95° C. for 6-7 hours under nitrogen atmosphere. Cooled the mass temperature to 25-30° C. 200.0 ml of DM water was charged. Stirred the mass for 20-30 min, and settled the mass for 15-20 min. Separated the top organic layer and kept aside. Charged the aqueous layer into a extraction flask. Compound was extracted with 3×300 ml of toluene. Combined the total organic layers were charged into a conical flask. Organic layer was dried with 50 g of sodium sulphate. Charged 10.0 g of activated carbon. Raised the mass temperature to 50-55° C. Maintained the mass temperature at 50-55° C. for 30-45 min. Filtered the sodium sulphate and carbon through hyflow bed and washed the sodium sulphate and carbon with 250.0 ml of toluene. Filtrate was charged into a flask and distilled off toluene completely under high vacuum, at mass temperature not crossing 65° C. Cooled the mass temperature to 25-30° C. 100.0 ml of isopropyl ether was charged. Stirred the mass temperature at 25-30° C. for 45-60 min. Filtered the solid and solid was washed with 25.0 ml of isopropyl ether. Compound was dried at 50-55° C. Obtained 22.40 g (79.85% of yield by theory) of light yellow coloured product.

Melting range: 218.1° C.-219.2° C.

HPLC purity 96.5%.

Spectral data : FT-IR (KBr): 3408, 2927, 2233, 1614, 1578, 1549, 1502, 1357, 1290, 1230, 1175, 981, 882, 843, 822, 663, 569, 494.

$^1$H NMR (DMSO-$d_6$) δ value (ppm): 4.04 (s) 2(O—CH3) (6H), 7.30 (s) Ar-Ha (1H), 7.51 (s )Ar-Hb, 9.23 (s) Ar-Hc (1H)

$^{13}$CNMR δ Value (ppm): 56.70 (2C), 100.88 (1C), 106.67 (1C), 114.92 (1C), 120.82 (1C), 137.61 (1C), 148.83 (1C), 152.57 (1C), 153.0 (1C), 157.62 (1C).

Mass: 217.22 [M+2], 216.21 [M+1]

30
1d) Preparation of 6,7-dimethoxy-4-(1H-tetrazol-5-yl)quinazoline

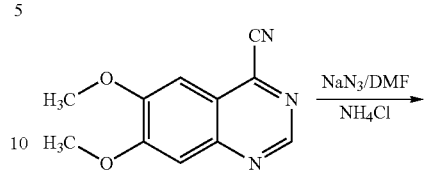

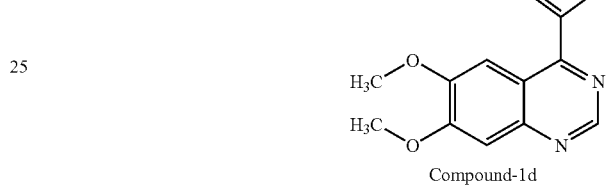
Compound-1d

Experimental Procedure: 400.0 ml of dimethyl formamide and 20.0 g (0.09 mol) of 4-cyano-6,7-dimethoxy-quinazoline were charged into a 1.0 L 4necked round bottom flask, connected to a mechanical stirrer, thermometer socket and condenser under nitrogen atmosphere. 6.80 g (0.10 mol) of Sodium azide and 5.50 g (0.10 mol) of ammonium chloride were charged at 25-35° C. Stirred the mass for 15-20 min at 25-35° C. Stirred the mass for 15-20 min at 25-35° C. Reaction mass temperature was raised to 110-115° C. Maintained the mass temperature at 110-115° C. for 8-9 hours. Inorganic solid was filtered at 110-115° C. and the filtrate was collected into a conical flask. Cooled the filtrate to 25-30° C. 4000.0 ml of ethyl acetate was charged into a 5.0 L 4necked round bottom flask, connected to a mechanical stirrer, thermometer socket and addition flask. Reaction mass of dimethyl formamide solution was added to ethyl acetate solution under stirring. Maintained the mass temperature at 25-30° C. for 60-90 min. Cooled the mass temperature to 0-5° C. Maintained the mass temperature at 0-5° C. for 150-180 min. Filtered the solid and solid was washed with 100.0 ml of ethyl acetate. Compound was dried at 25-30° C. under vacuum. Obtained 14.20 g (yield is 59.16% by theory) of product Melting range 207.2° C.

HPLC purity: 98.6%.

Spectral data: FT-IR (KBr): 3421, 2986, 1615, 1552, 1507, 1478, 1431, 1342, 1242, 998, 965, 799, 659, 450

$^1$H NMR (DMSO-$d_6$) δ value (ppm): 3.92 (s) 2(O—CH3) (6H), 7.34 (s) Ar-Ha (1H), 8.20 (broad) NH (1H), 8.97 (s) Ar-Hb (1H), 9.07 (s) Hc (1H)

$^{13}$CNMR δ value (ppm): 56.36 (2C), 103.28 (1C), 106.72 (1C), 117.39 (1C), 146.81 (1C), 149.87 (1C), 151.43 (1C), 152.58 (1C), 154.65 (1C), 156.54 (1C).

Mass: 258.14 [M], 257.18 [M−1]

I. Preparation of 6,7-Dimethoxy-4-(1-(3-nitrobenzyl)-1H-tetrazole-5-yl)quinazoline (Compound-IV)

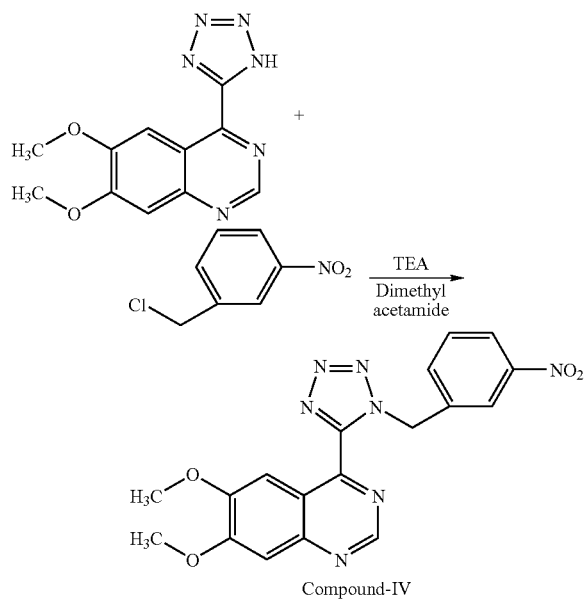

Compound-IV

Experimental Procedure: 150.0 ml of N,N-dimethyl acetamide and 10.0 g (0.038 mol) of 6,7-dimethoxy-4-(1H-tetrazol-5-yl)quinazoline were charged into a 500 ml of 4 necked round bottom flask, connected to a mechanical stirrer, thermometer socket, condenser and addition flask under mild nitrogen atmosphere. 6.0 g (0.06 mol) of triethyl amine was added at 25-30° C. Stirred the mass for 15-20 min at 25-30° C. Reaction mass temperature was raised to 50-55° C. Maintained the mass temperature at 50-55° C. for 15-20 min. 3-Nitro benzyl chloride solution {4.50 g (0.026 mol) of 3-nitro benzyl chloride was dissolved in 37.50 ml of N,N-dimethyl acetamide} was added slowly at 50-55° C. over a period of 30-45 min. Maintained the mass temperature at 50-55° C. for 15-20 min. Raised the mass temperature to 80-85° C. Maintained the mass temperature at 80-85° C. for 7-8 hours. Cooled the mass temperature to 25-30° C. 1875.0 ml of methanol was charged into a 3.0 L 4 necked round bottom flask, connected to a mechanical stirrer, thermometer socket, condenser and addition flask at 25-30° C. Reaction mass of dimethyl acetamide solution was added to methanol solution at 25-30° C. during 60-90 min under stirring. Maintained the mass temperature at 25-30° C. for 60-90 min. Cooled the mass temperature to 0-5° C. Maintained the mass temperature at 0-5° C. for 150-180 min. Solid was filtered solid, washed with 50.0 ml of methanol. Compound was dried at 25-30° C. 11.80 g (yield 77.6% by theory) Of dried compound-I is obtained.

Melting range 221.2° C.-222.2° C.

HPLC purity: 97.24%.

Spectral data: FT-IR (KBr): 3428, 3105, 2940, 1615, 1519, 1504, 1427, 1359, 1324, 1241, 1151, 1118, 1001, 966, 868, 851, 728, 658, 631, 561, 470.

$^1$H NMR (DMSO-$d_6$) δ value (ppm): 3.92 (s) 2(O—CH3) (6H), 6.22 (s) (CH2) 2H), 7.51 (s) Ar-Ha (1H), 7.64-7.67 (t) Ar-Hb (1H), 7.87-7.89 (d) (1H), 8.14-8.18 (t) Ar—He (1H), 8.32 (s) Ar—Hf (1H), 9.28 (s) Hg (1H).

$^{13}$CNMR δ value (ppm): 51.56 (1C), 56.45 (2C), 103.27 (1C), 106.80 (1C), 118.51 (1C), 123.16 (1C), 123.32 (1C), 130.23 (1C), 135.15 (1C), 136.92 (1C), 147.55 (1C), 147.73, (1C), 149.63 (1C), 151.10 (1C), 151.40 (1C), 152.21 (1C), 156.68 (1C).

Mass: 395.2 [M+2], 394.2 [M+1]

Example-2

2. Preparation of 6,7-Dimethoxy-4-(1-(3-aminobenzyl)-1H-tetrazol-5-yl)quinazoline (Compound-V)

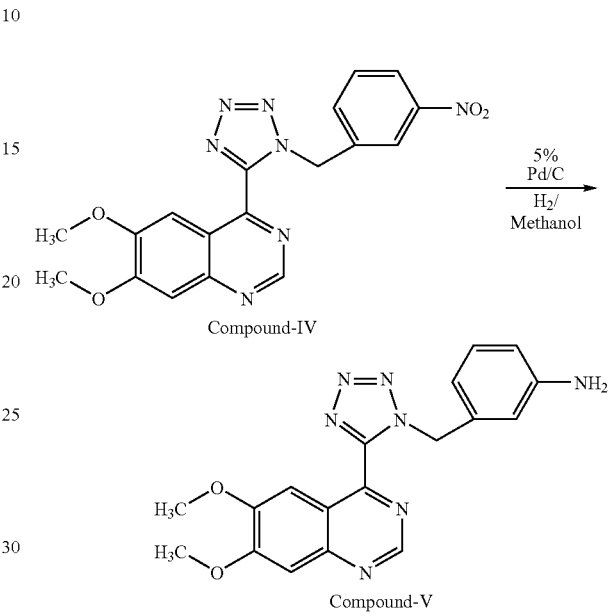

Compound-V

Experimental Procedure: 400.0 ml dimethyl formamide and 10.0 g (0.025 mol) of 6,7-dimethoxy-4-(1-(3-nitrobenzyl)-1H-tetrazol-5-yl)quinazoline suspension was charged into a 1.0 L hydrogenator kettle at 25-30° C. 5.0 g of 5% palladium carbon (50% wet) was charged under nitrogen atmosphere. Hydrogenation was carried at 35-40 psi under oscillation at 25-30° C. Maintained the Hydrogen gas pressure (35-40 psi) till the Hydrogen gas uptake is stopped. Filtered the catalyst through hyflow bed under nitrogen atmosphere. The catalyst was washed with 50.0 ml of dimethyl formamide under nitrogen atmosphere. Filtrate was collected into a single neck RB flask, and distilled off dimethyl formamide completely under high vacuum at below 60° C. Cooled the mass temperature to 25-30° C. and released the vacuum, 50.0 ml of hexane was charged and stirred the mass for 45-60 min at 25-30° C. Filtered the solid, washed with 25.0 ml of hexane. Compound was dried at 25-30° C. 8.40 g of crude product is obtained. The crude product was purified by column chromatography in a silica column using mobile phase as ethylacetate and hexane mixture. Obtained 5.20 g (56.3% yield by theory) of product with HPLC purity of 99.3%.

Spectral data: FT-IR (KBr): 3430, 3008, 2930, 1613, 1551, 1501, 1429, 1375, 1320, 1236, 1150, 1001, 963, 871, 845, 797, 775, 693, 657, 627, 446.

$^1$H NMR (DMSO-$d_6$) δ value (ppm): 3.92 (s) (O—CH3) (3H), 4.03 (s) (O—CH$_3$) (3H), 5.07 (s) CH2 (2H), 5.95-5.98 (s) NH2 (2H), 6.34-6.43 (m) Ar-Ha,Hb,Hc (3H), 6.86-6.89 (t) Ar-Hd (1H), 7.50 (s) Ar—He (1H), 8.04 (s) Ar—Hf (1H), 9.31 (s) Hg (1H)

$^{13}$CNMR δ value (ppm): 51.56 (1C), 56.45 (2C), 103.07 (1C), 106.80 (1C), 112.91 (1C), 113.61 (1C), 115.07 (1C), 118.49 (1C), 129.08 (1C), 129.08 (1C), 135.31 (1C), 147.69 (1C), 148.95 (1C), 150.63 (1C), 151.42 (1C), 152.31 (1C), 156.76 (1C).

Mass: 365.3 [M+2], 364.1 [M+1]

II. HCl: Preparation of 6,7-Dimethoxy-4-(1-(3-aminobenzyl)-1H-tetrazol-5-yl)quinazoline hydrochloride salt

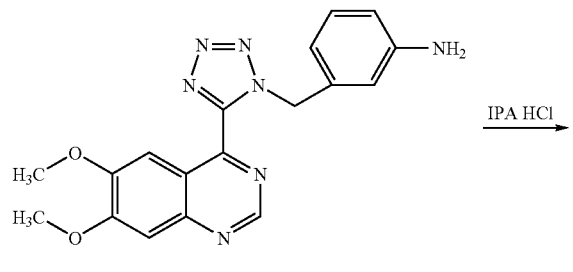

IPA HCl

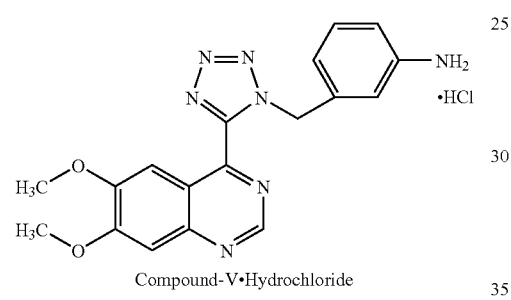

Compound-V·Hydrochloride

Experimental Procedure: Charged 200.0 ml of methylene chloride and 5.0 g (0.013 mol) of 6,7-Dimethoxy-4-(1-(3-aminobenzyl)-1H-tetrazol-5-yl)quinazoline into a 500 ml of 4 necked round bottom flask, connected to a mechanical stirrer, thermo meter socket and condenser at 25-30° C. Stirred the mass for 15 min. After dissolution is clear, 6.0 g of IPA HCl was added. Stirred the mass for 1 hour. Methylene chloride was distilled of up to remaining the total mass volume 30.0 ml. 200 ml of hexane was added. Stirred the mass for 1 hour. Filtered the solid and solid was washed with 30.0 ml of hexane. Compound was dried at 55-60° C. Obtained light yellow coloured dry compound 4.80 g (yield is 87.2% by theory). Melting range 234.8-236.3° C. Product purity: 99.5% by HPLC.

Spectral data: FT-IR (KBr): 3424, 3227, 3094, 3052, 2978, 2878, 2746, 1665, 1595, 1508, 1471, 1435, 1411, 1352, 1312, 1286, 1260, 1239, 1205, 1131, 1110, 1065, 1050, 917, 885, 854, 827, 778, 721, 684, 534, 476.

$^1$H NMR (DMSO-$d_6$) δ value (ppm): 3.94 (s) (O—CH3) (3H), 4.03 (s) (O—CH3) (3H), 5.07 (s) CH2 (2H), 6.09 (s) NH2 (2H), 6.34-6.43 (m) Ar-Ha,Hb,Hc (3H), 6.86-6.89 (t) Ar-Hd (1H), 7.50 (s) Ar—He (1H), 8.04 (s) Ar—Hf (1H), 9.31 (s) Hg (1H)

$^{13}$CNMR δ value (ppm): 51.95 (1C), 56.43 (1C), 103.26 (1C), 106.75 (1C), 118.35 (1C), 122.77 (1C), 127.54 (1C), 130.01 (1C), 132.79 (1C), 136.68 (1C), 147.68 (1C), 150.9391C), 151.37 (1C), 152.28 (1C), 156.60 (1C).

Mass: 400.3 [M+1], 398.3 [M−1].

Example-3

Preparation of 6,7-dimethoxy-4-[1-(1-methyl-1H-imidazol-2-ylmethyl)-1H-tetrazol-5-yl]-quinazoline (Formula-VI)

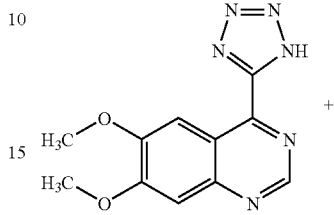

+

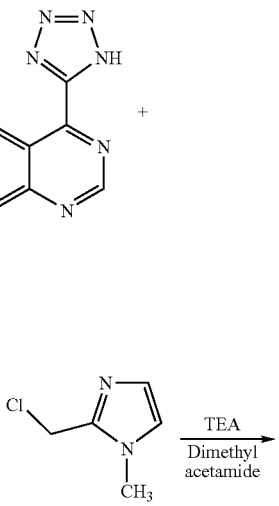

TEA
Dimethyl acetamide

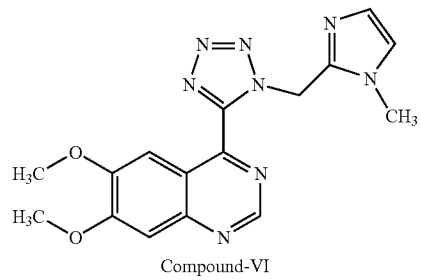

Compound-VI

Experimental Procedure: 50.0 ml of N,N-dimethyl acetamide and 5.0 g (0.019 mol) of 6,7-dimethoxy-4-(1H-tetrazol-5-yl)quinazoline were charged into a 250 ml of 4necked round bottom flask, connected to a mechanical stirrer, thermometer socket, condenser and addition flask under mild nitrogen atmosphere. 3.80 g (0.038 mol) of triethyl amine was added at 25-30° C. Stirred the mass for 15-20 min at 25-30° C. Reaction mass temperature was raised to 50-55° C. Maintained the mass temperature at 50-55° C. for 15-20 min. 2-chloro methyl -1-methyl-imidazole solution [2.50 g (0.019 mol) 2-chloro methyl -1-methyl-imidazole was dissolved in 25.0 ml of N,N-dimethyl acetamide] was added slowly at 50-55° C. for 30-45 min. Maintained the mass temperature at 50-55° C. for 15-20 min. Raised the mass temperature to 80-85° C. Maintained the mass temperature at 80-85° C. for 7-8 hours. N,N-dimethyl acetamide was completely distilled under vacuum. Crude compound was purified by the column chromatography by using hexane and ethyl acetate. Obtained pure compound weight 2.40 g (yield 35.2% by theory).

Spectral data: Mass: 353 [M+1], 352.0 [M]

Example-4

Preparation of 6,7-dimethoxy-4-[1-(pyridine-2-ylmethyl)-1H-tetrazol-5-yl]-quinazoline

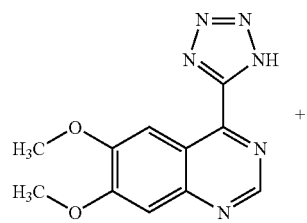

+

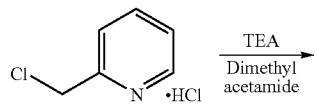

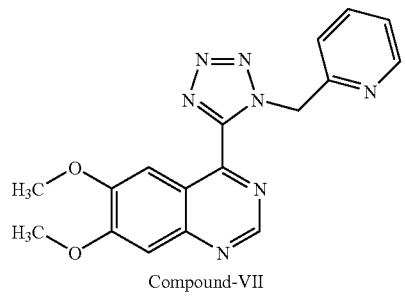

Compound-VII

Experimental Procedure: 50.0 ml of N,N-dimethyl acetamide and 5.0 g (0.019 mol) of 6,7-dimethoxy-4-(1H-tetrazol-5-yl)quinazoline were charged into a 250 ml of 4 necked round bottom flask, connected to a mechanical stirrer, thermometer socket, condenser and addition flask under mild nitrogen atmosphere. 3.80 g (0.038 mol) of triethyl amine was added at 25-30° C. Stirred the mass for 15-20 min at 25-30° C. Reaction mass temperature was raised to 50-55° C. Maintained the mass temperature at 50-55° C. for 15-20 min. 2-chloro methylpyridine hydrochloride solution [3.20 g (0.019 mol) 2-chloro methylpyridine hydrochloride was dissolved in 25.0 ml of N,N-dimethyl acetamide] was added slowly at 50-55° C. for 30-45 min. Maintained the mass temperature at 50-55° C. for 15-20 min. Raised the mass temperature to 80-85° C. Maintained the mass temperature at 80-85° C. for 7-8 hours. N,N-dimethyl acetamide was completely distilled off under vacuum. Crude compound was purified by the column chromatography by using hexane and ethyl acetate. Obtained 1.90 g (yield 28.0% by theory) of pure compound weight.

Spectral data: Mass: 350 [M+1], 349.0 [M]

Example-5 to 8

The analogous compounds of 3,4-diethoxy derivatives of quinazoline compounds VIII to XI and the their intermediates VIII a to VIII d are prepared as per the procedure mentioned in examples-1a to 1d and IV to VII i) Mass Spectral Properties of Compounds VIII a to VIII d

| Compound Number | Molecular formula | Molecular weight | Mass peaks Peak-i | Peak-ii |
|---|---|---|---|---|
| VIII a | $C_{12}H_{13}N_2O_2Cl$ | 252.5 | 253.7 [M + 1] | 252.5 [M] |
| VIII b | $C_{15}H_{22}N_3O_2Cl$ | 311.5 | 312.6 [M + 1] | 311.6 [M] |
| VIII c | $C_{13}H_{13}N_3O_2$ | 243.0 | 245.2 [M + 2] | 244.2 [M + 1] |
| VIII d | $C_{13}H_{14}N_6O_2$ | 286.0 | 286.3 [M] | 285.1 [M − 1] | ii) Mass Spectral Properties of Compounds VIII to XI

| Compound Number | Molecular formula | Molecular weight | Mass peaks [M + 2] | [M + 1] |
|---|---|---|---|---|
| VIII | $C_{20}H_{19}N_7O_4$ | 421.0 | 423.4 | 422.4 |
| IX | $C_{20}H_{21}N_7O_2$ | 391.0 | 393.4 | 392.4 |
| X | $C_{18}H_{20}N_8O_2$ | 380.0 | 382.4 | 381.4 |
| XI | $C_{19}H_{19}N_7O_2$ | 377.0 | 379.4 | 378.4 |

Example-9 to 12

The analogous compounds of 3,4-dipropoxy derivatives of quinazoline compounds XII to XV and the their intermediates XIIa to XIId are prepared as per the procedure mentioned in examples-1a to 1d and IV to VII iii) Mass Spectral Properties of Compounds XII a to XII d

| Compound Number | Molecular formula | Molecular weight | Mass peaks Peak-i | Peak-ii |
|---|---|---|---|---|
| XII a | $C_{14}H_{17}N_2O_2Cl$ | 280.5 | 281.7 [M + 1] | 280.7 [M] |
| XII b | $C_{17}H_{26}N_3O_2Cl$ | 339.5 | 340.6 [M + 1] | 339.6 [M] |
| XII c | $C_{15}H_{17}N_3O_2$ | 271.0 | 273.2 [M + 2] | 272.2 [M + 1] |
| XII d | $C_{15}H_{18}N_6O_2$ | 314.0 | 314.3 [M] | 313.1 [M − 1] | iv) Mass Spectral Properties of Compounds XII to XV

| Compound Number | Molecular formula | Molecular weight | Mass peaks [M + 2] | [M + 1] |
|---|---|---|---|---|
| XII | $C_{22}H_{23}N_7O_4$ | 449.0 | 451.4 | 450.4 |
| XIII | $C_{22}H_{25}N_7O_2$ | 419.0 | 421.4 | 420.4 |
| XIV | $C_{20}H_{24}N_8O_2$ | 408.0 | 410.4 | 409.4 |
| XV | $C_{21}H_{23}N_7O_2$ | 405.0 | 407.4 | 406.4 |

We claim:
1. A 4-(tetrazol-5-yl)-quinazoline of formula-I

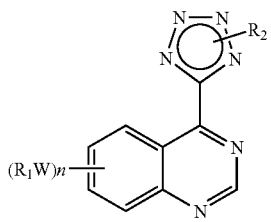

Formula-I or a pharmaceutically acceptable salt thereof;
where
n is 1, 2, or 3;
W is selected from a single bond, —O—, —S—, —$COR_6$—, —NH—, —SO—, —$SO_2$—, —$NR_6CO$—, —$CONR_6$—, —$SO_2NR_7$—, —$NR_7SO_2$—, or —$NR_8$— (wherein $R_6$, $R_7$ and $R_8$ each independently represents hydrogen, $C_1$-$C_6$alkyl, $C_3$-$C_6$cycloalkyl, $C_2$-$C_5$alkenyl, $C_2$-$C_5$alkynyl;
each $R_1$ is independently selected from the group consisting of hydrogen, halogen, hydroxy, amino, hydroxylamino, carboxy, nitro, guanidino, ureido, cyano, trifluoromethyl, azido;
each $R_1$ is independently selected from the group consisting of $C_1$-$C_6$alkyl, $C_3$-$C_6$ cycloalkyl, aryl, $R_3$-substituted aryl, aryl $C_1$-$C_6$alkoxy, $C_3$-$C_6$cycloalkoxy, ($C_1$-$C_6$)alkanoyloxy, $R_5$-aryloxy, $C_1$-$C_6$alkoxy $C_1$-$C_6$alkyloxy, $C_1$-$C_6$alkoxy-$C_3$-$C_6$cycloalkyloxy, $C_1$-$C_6$alkoxy-$R_5$-aryloxy, N-mono($C_1$-$C_6$)alkylamino, N,N-di($C_1$-$C_6$)alkylamino, formamido, amido, acetamido, $C_1$-$C_6$-alkoxyamino, hydrazine, trifluoromethoxy, alkenyl, alkynyl, aryl, or fused aryl; where $R_3$ is selected from $C_1$-$C_6$ alkyl, $C_3$-$C_6$ cycloalkyl, aryl, and aralkyl; $R_5$ is independently hydrogen or $R_4$; and $R_4$ is $C_1$-$C_4$ alkyl;
each $R_1$ is independently selected from $R_9$-substituted by halogen, hydroxy, amino, hydroxylamino, carboxy, nitro, guanidino, ureido, cyano, trifluoromethyl, azido;
wherein $R_9$ is selected from the group consisting of $R_4$, —$OR_5$, —$NR_5R_5$, —$C(O)R_6$, —$NHOR_4$, —$OC(O)R_5$, P and -$QR_4$; $R_6$ is $R_3$, —$OR_5$ or —$NR_5R_5$; P is selected from piperidino, morpholino, pyrrolidino, 4-$R_3$-piperazin-1-yl, imidazol-1-yl, 4-pyridin-1-yl, —($C_1$-$C_4$alkylene)($CO_2H$), phenoxy, phenyl, phenylsulfonyl, $C_2$-$C_4$alkenyl, and —($C_1$-$C_4$alkylene)C(O)$NR_5R_5$; and Q is S, SO, or $SO_2$;
or each $R_1$ is independently selected from —$NHSO_2R_4$, phthalimido-($C_1$-$C_4$)-alkylsulfonylamino, benzamido, benzenesulfonylamino, 3-phenylureido, 2-oxopyrrolidin-1-yl, 2,5-dioxopyrrolidin-1-yl, and $R_4$—($C_2$-$C_4$)-alkanoylamino; optionally substituted by 1 or 2 substituents independently selected from halo, $C_1$-$C_4$alkyl, cyano, methanesulfonyl and $C_1$-$C_4$alkoxy;
$R_2$ is hydrogen or selected from the group consisting of $C_1$-$C_6$alkyl, $C_3$-$C_6$cycloalkyl, ($C_1$-$C_6$)carbonyloxyalkyl, $R_4$-aryl, $R_4$-aryl substituted with ($R_{11}$)m, where m=1, 2 or 3 and $R_{11}$ is independently selected from the group consisting of hydrogen, halogen, hydroxy, hydroxylamino, carboxy, nitro, guanidino, ureido, cyano, trifluoromethyl, azido, or $R_3$ (as defined above), $R_4$-fused aryl, $R_4$—$C_1$-$C_6$alkyloxy, $R_4$—$C_1$-$C_6$alkyloxy substituted with ($R_{11}$)m, $R_4$—$C_3$-$C_6$cycloalkyloxy, $R_4$—$C_3$-$C_6$cycloalkyloxy substituted with ($R_{11}$)m, $C_1$-$C_6$alkoxy-$R_5$-aryloxy, $C_1$-$C_6$alkoxy-$R_5$-aryloxy substituted with ($R_{11}$)m, N-mono($C_1$-$C_6$)alkylamino, N-mono($C_1$-$C_6$)alkylamino substituted with ($R_{11}$)m, N,N-di($C_1$-$C_6$)alkylamino, N,N-di($C_1$-$C_6$)alkylamino substituted with ($R_{11}$)m, formamido, amido, acetamido, $C_1$-$C_6$alkoxyamino, hydrazine, trifluoromethoxy, $C_2$-$C_6$alkenyl, $C_2$-$C_6$alkenyl substituted with ($R_{11}$)m, or $C_2$-$C_6$alkynyl, $C_2$-$C_6$alkynyl substituted with ($R_{11}$)m.

2. A pharmaceutical composition comprising a therapeutically effective amount of the compound of claim 1 and a pharmaceutically acceptable carrier.

3. The compound of claim 1, wherein each $R_1$ is independently $C_1$-$C_6$ branched alkyl, $C_2$-$C_6$ branched alkenyl, or $C_2$-$C_6$ branched alkynyl.

4. The compound of Formula IV, Formula V, or a pharmaceutically acceptable salt thereof:

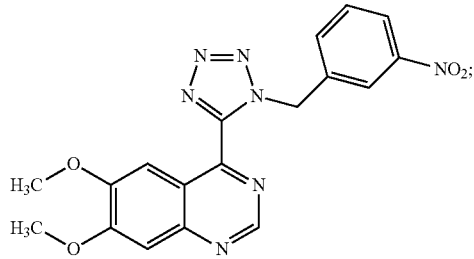

Formula-IV

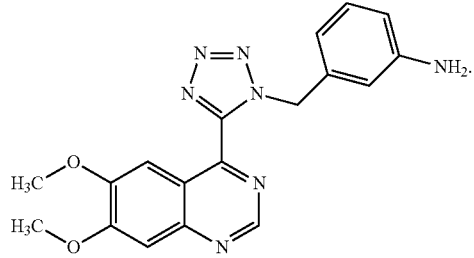

Formula-V

5. A 4-(tetrazol-5-yl)-quinazoline selected from:
a) 6,7-Dimethoxy-4-(1-(3-nitrobenzyl)-1H-tetrazol-5-yl)quinazoline;
b) 3-((5-(6,7-dimethoxyquinazolin-4-yl)-1H-tetrazol-1-yl)methyl)aniline;
c) 6,7-dimethoxy-4-(1-((1-methyl-1H-imidazol-2-yl)methyl)-1H-tetrazol-5-yl)quinazoline;
d) 6,7-dimethoxy-4-(1-(pyridin-2-ylmethyl)-1H-tetrazol-5-yl)-quinazoline;
e) 6,7-diethoxy-4-(1H-tetrazol-5-yl)quinazoline;
f) 6,7-diethoxy-4-(1-(3-nitrobenzyl)-1H-tetrazol-5-yl)quinazoline;
g) 3-((5-(6,7-diethoxyquinazolin-4-yl)-1H-tetrazol-1-yl)methyl)aniline;
h) 6,7-diethoxy-4-(1-((1-methyl-1H-imidazol-2-yl)methyl)-1H-tetrazol-5-yl)quinazoline;
i) 6,7-diethoxy-4-(1-(pyridin-2-ylmethyl)-1H-tetrazol-5-yl)-quinazoline;
j) 6,7-dipropoxy-4-(1H-tetrazol-5-yl)quinazoline;
k) 6,7-di-n-propoxy-4-(1-(3-nitrobenzyl)-1H-tetrazol-5-yl)quinazoline;
l) 3-((5-(6,7-di-n-propoxyquinazolin-4-yl)-1H-tetrazol-1-yl)methyl)aniline;
m) 4-(1((1-methyl-1H-imidazol-2-yl)methyl)-1H-tetrazol-5-yl) 6,7-di-n-propoxy quinazoline;
n) 6,7-di-n-propoxy-4-(1-(pyridin-2-ylmethyl)-1H-tetrazol-5-yl)-quinazoline; or
a pharmaceutically acceptable salt thereof.

* * * * *